US012629052B1

(12) United States Patent
　　Alsaif et al.

(10) Patent No.: US 12,629,052 B1
(45) Date of Patent: May 19, 2026

(54) TOOL ASSEMBLY AND METHOD FOR MEASURING AT LEAST ONE FACIAL FEATURE OF A PATIENT

(71) Applicant: KING SAUD UNIVERSITY, Riyadh (SA)

(72) Inventors: Rand Fahad Alsaif, Riyadh (SA); Rayan Bakur Alkurdi, Riyadh (SA); Yasser Fahad Alrayyes, Riyadh (SA); Reham Nasser Al Jasser, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/413,260

(22) Filed: Dec. 9, 2025

(51) Int. Cl.
　　　*A61B 5/107* 　　　(2006.01)
　　　*A61B 5/00* 　　　(2006.01)

(52) U.S. Cl.
　　　CPC .......... *A61B 5/1072* (2013.01); *A61B 5/1075* (2013.01); *A61B 5/4547* (2013.01); *A61B 5/4552* (2013.01)

(58) Field of Classification Search
　　　CPC ....... A61C 19/04; A61C 11/022; A61C 11/06; A61C 11/081; A61C 11/088; A61C 19/043; A61C 19/045; A61C 19/05; G01B 3/56; G01B 3/04; A61B 5/1072; A61B 2560/0431; B43L 7/10
　　　See application file for complete search history.

(56) References Cited

U.S. PATENT DOCUMENTS 1,183,977 A * 5/1916 Hoefle ...................... G01B 3/56
　　　　　　　　　　　　　　　　355/126
3,991,474 A * 11/1976 Rath ......................... B43L 7/12
　　　　　　　　　　　　　　　　33/462

5,461,794 A 　10/1995 Huang
7,254,898 B1 　8/2007 Armstrong
10,080,637 B2 　9/2018 Bakeman
10,835,359 B2 　11/2020 Wagner
2006/0090360 A1 * 　5/2006 Shapiro .................... G01B 3/04
　　　　　　　　　　　　　　　　33/473
2011/0136073 A1 　6/2011 Basta

FOREIGN PATENT DOCUMENTS

CN 　　　108542537 B 　　8/2024

OTHER PUBLICATIONS

Dawadi, et al. "Clinical and psychological impact of lip repositioning surgery in the management of excessive gingival display." The Saudi Dental Journal 36.1 (2024): 84-90.

* cited by examiner

*Primary Examiner* — Scott Luan

(74) *Attorney, Agent, or Firm* — Nath, Goldberg & Meyer; Joshua B. Goldberg

(57) 　　　　　　ABSTRACT

A method of using a tool assembly to measure at least one facial feature of a patient includes obtaining at least two slidable pins; removably attaching the at least two slidable pins to the first slot of the primary removably attachable tool; placing the tool assembly in front of the patient's face; sliding a first of the at least two slidable pins along the first slot towards a first region of the patient's face; sliding a second of the at least two slidable pins along the first slot towards a second region of the patient's face; and measuring the at least one facial feature of the patient based on a height difference between the first of the at least two slidable pins and the second of the at least two slidable pins.

19 Claims, 15 Drawing Sheets

TOOL ASSEMBLY AND METHOD FOR MEASURING AT LEAST ONE FACIAL FEATURE OF A PATIENT

BACKGROUND

Field

The disclosure of the present patent application relates to a tool assembly, and particularly to a tool assembly and a method of measuring at least one facial feature of a patent.

Description of Related Art

A smile plays a significant role in a patient's facial appearance and confidence. As more people seek treatments to improve their aesthetic appearance, one common concern is excessive gingival display (EGD), commonly known as a gummy smile. EGD is characterized by visible excess gum tissue above the upper teeth, especially when more than 4 mm of gum is visible upon smiling. Although generally considered an aesthetic concern rather than a pathological one, EGD can significantly impact a patient's confidence, psychosocial well-being, and perceived facial harmony. The etiology of EGD is multifactorial and may involve dental, gingival, skeletal, and muscular components, either in isolation or combination.

One common cause of EGD is altered passive eruption (APE), a developmental condition characterized by incomplete apical migration of the gingival margin after tooth eruption. In APE, the clinical crowns of the teeth appear shortened due to excessive gingival coverage of the anatomic crown, despite normal tooth eruption and alveolar bone positioning.

Gingival overgrowth, or gingival hyperplasia, is another contributing factor. This condition involves an abnormal increase in gingival tissue volume, often due to inflammatory, drug-induced, or hereditary factors. Gingival enlargement can lead to the concealment of tooth structure and an increase in gingival display during smiling.

Muscular factors, particularly involving the upper lip, can also contribute to EGD. A hyperactive upper lip results from over contraction of the levator labii superioris, levator labii superioris alaeque nasi, and zygomaticus minor muscles during smiling. This hyperactivity elevates the upper lip excessively, revealing a disproportionate amount of gingiva.

Skeletal discrepancies are another recognized etiology. Vertical maxillary excess (VME), characterized by an increased vertical dimension of the maxilla, can cause the entire upper jaw to be positioned lower relative to the rest of the facial skeleton. As a result, the gingiva is exposed to a greater extent during smiling, even with normal lip and tooth proportions.

Additionally, a short upper lip, whether congenital or acquired, can exacerbate EGD by reducing the vertical coverage of the maxillary anterior dentition and gingiva at rest and during smiling. The combination of a short upper lip and increased muscular activity often amplifies gingival exposure.

Current approaches for managing EGD include surgical, orthodontic, and minimally invasive techniques. Surgical methods such as crown lengthening, lip repositioning, and orthognathic surgery address the underlying dental, soft tissue, or skeletal causes. However, these interventions can be invasive, costly, and associated with prolonged recovery or aesthetic limitations. Minimally invasive alternatives, including the use of neuromodulators or laser-assisted gingival contouring, provide temporary or partial correction but often fail to address the multifactorial etiology comprehensively. Wrong diagnosis for etiology can lead to unnecessary treatments, patient's dissatisfaction, and wasting time including resources.

In light of the above, a need remains for a diagnostic tool that can accurately identify the underlying cause of EGD for solving the aforementioned problems.

SUMMARY

The present subject matter relates to a tool assembly which, in one embodiment, includes a primary removably attachable tool comprising a first slot, a second slot, and a slidable primary upper plate removably attached to the second slot, wherein the slidable primary upper plate is configured to slide along the second slot; a secondary removably attachable tool comprising a third slot and a slidable secondary upper plate removably attached to the third slot, the slidable secondary upper plate configured to slide along the third slot, and wherein the secondary removably attachable tool, attached to the slidable primary upper plate, is configured to slide along the second slot.

In an embodiment, the primary removably attachable tool and/or the secondary removably attachable tool can include a ruler.

In another embodiment, the first slot and the second slot of the primary removably attachable tool can be parallel to each other, and the third slot of the secondary removably attachable tool can be perpendicular to the first slot and the second slot of the primary removably attachable tool.

In an additional embodiment, the primary removably attachable tool can include a first portion, a second portion, a third portion, and a fourth portion, wherein an entire first length of the first slot can extend within the second portion and the third portion of the primary removably attachable tool, and wherein an entire second length of the second slot can extend within the second portion of the primary removably attachable tool.

In a supplementary embodiment, the secondary removably attachable tool can include a first section, a second section, a third section, and a fourth section, wherein the first section of the secondary removably attachable tool can include a primary transparent recess component, and wherein the attachment of the secondary removably attachable tool to the slidable primary upper plate can be via the primary transparent recess component.

In an embedment, the tool assembly can further include at least one slidable pin removably attached to the first slot of the primary removably attachable tool, and wherein the at least one slidable pin can be configured to slide along the first slot.

In another embodiment, a portion of the at least one slidable pin can be configured to be capable of sliding above and past the slidable primary upper plate.

In an additional embodiment, the at least one slidable pin can include at least two of a first slidable pin, a second slidable pin, a third slidable pin, a fourth slidable pin, and a fifth slidable pin, and wherein each of the first slidable pin, the second slidable pin, the third slidable pin, the fourth slidable pin, and the fifth slidable pin can be configured to be slidably positioned along various parts of a patient's face.

In a supplementary embodiment, the fourth slidable pin can be longer than the first slidable pin, the second slidable pin, the third slidable pin, and the fifth slidable pin.

In a further embodiment, the tool assembly can further include a gauge which can be configured to be removably attached to the slidable secondary upper plate.

In an embodiment, the gauge can include an incisor proportion gauge.

In another embodiment, the incisor proportion gauge can include a secondary transparent recess component.

In an additional embodiment, the attachment of the incisor proportion gauge to the slidable secondary upper plate can be via the secondary transparent recess component.

In a further embodiment, the present subject matter relates to a method of using the above tool assembly to measure at least one facial feature of a patient, wherein the method includes obtaining at least two slidable pins; removably attaching the at least two slidable pins to the first slot of the primary removably attachable tool; placing the tool assembly in front of the patient's face; sliding a first of the at least two slidable pins along the first slot towards a first region of the patient's face; sliding a second of the at least two slidable pins along the first slot towards a second region of the patient's face; and measuring the at least one facial feature of the patient based on a height difference between the first of the at least two slidable pins and the second of the at least two slidable pins.

In an embodiment, the method can further include sliding a fourth of the at least two slidable pins towards a first position of an upper lip line of the patient while the patient's mouth is at rest; recording a first marking on the ruler of the primary removably attachable tool corresponding to the first position of the upper lip line of the patient; sliding the fourth slidable pin towards a second position of the upper lip line of the patient after the patient has smiled; recording a second marking on the ruler of the primary removably attachable tool corresponding to the second position of the upper lip line of the patient; and measuring another of the at least one facial feature of the patient based on a height difference between the first marking and the second marking on the ruler.

In another embodiment, the method can further include: sliding the secondary removably attachable tool near the patient's mouth as the slidable primary upper plate slides along the second slot; recording a third marking and a fourth marking on the ruler of the secondary removably attachable tool corresponding to a right buccal corridor and a left buccal corridor, respectively, of the patient's mouth as the patient is smiling; and measuring an additional one of the at least one facial feature of the patient based on a difference between the third marking and the fourth marking on the ruler of the secondary removably attachable tool.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
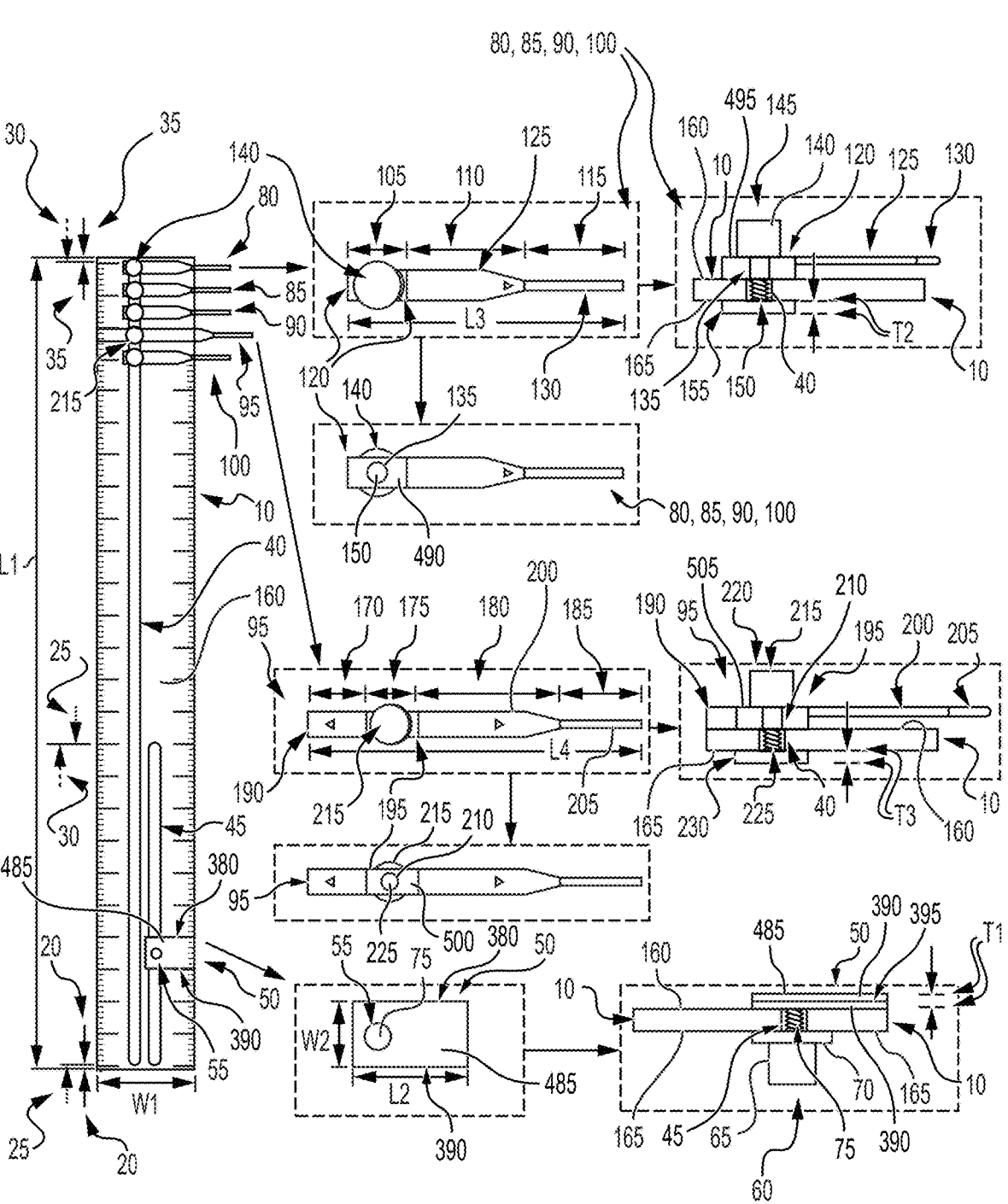
FIG. 1 depicts a primary removably attachable tool with various components attached thereto.

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Figure 6:
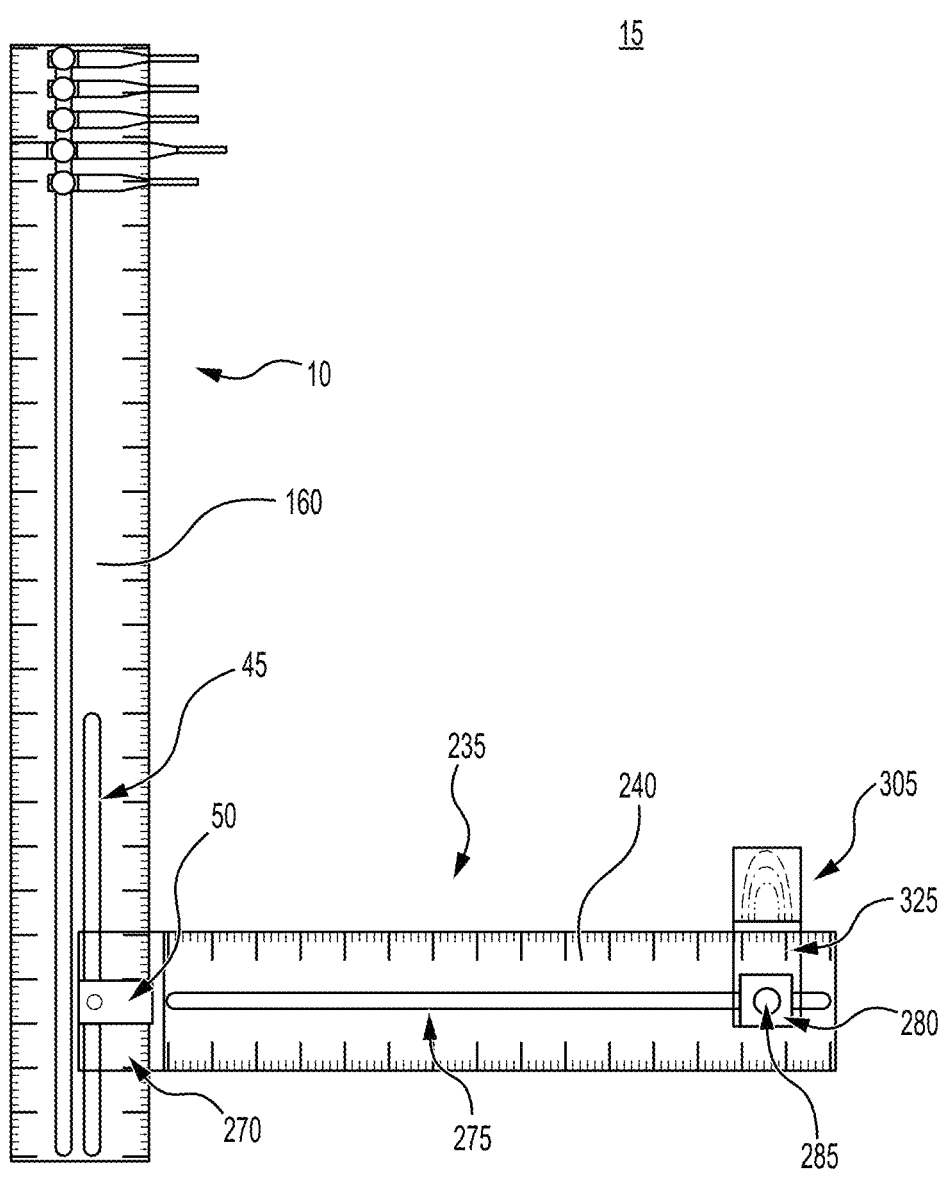
FIG. 6 depicts the attachments of the primary removably attachable tool, the secondary removably attachable tool, and the incisor proportion gauge to form a tool assembly.

FIG. 1 depicts, in a first embodiment, a primary removably attachable tool 10 which can be part of a tool assembly 15 as shown in FIG. 6. The primary removably attachable tool 10 can include a ruler with various markings representing numbers for measurement purposes. The primary removably attachable tool 10 can include a primary length L1 of about 250 mm and a primary width W1 of about 30 mm as shown in FIG. 1. Other primary lengths and widths for the primary removably attachable tool are further contemplated as within the scope of the present subject matter. The primary removably attachable tool 10 can include a first portion 20, a second portion 25, a third portion 30, and a fourth portion 35 as illustrated in FIG. 1.

The primary removably attachable tool 10, as seen in FIG. 1, can include a first slot 40 and a second slot 45. The first slot 40 can be parallel to the second slot 45. An entire first length of the first slot 40 can extend within the second portion 25 and the third portion 30 of the primary removably attachable tool 10. Likewise, an entire second length of the second slot 45 can extend within the second portion 25 of the primary removably attachable tool 10.

The primary removably attachable tool 10 can further include a slidable primary upper plate 50 as indicated in FIG. 1. The slidable primary upper plate 50 can include a secondary length L2 of about 15 mm and a secondary width W2 of about 10 mm. The slidable primary upper plate 50 can also include a primary threaded hole 55 located therein. Specifically, the primary threaded hole 55 can extend an entire first thickness T1 of the slidable primary upper plate 50 with a terminal end on a top periphery 485 of the slidable primary upper plate 50 as displayed in FIG. 1.

Figure 5:
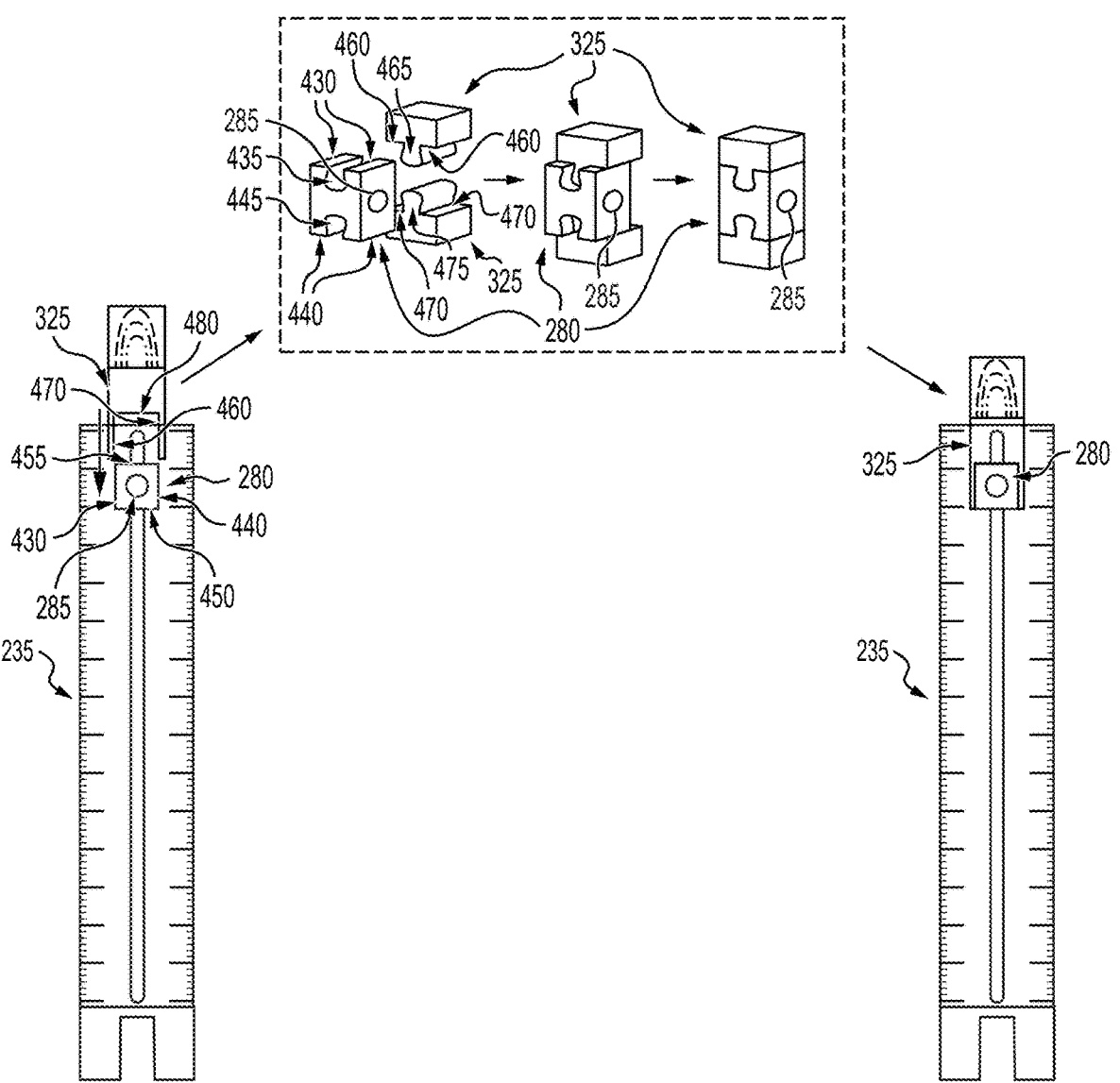
FIG. 5 depicts sliding attachment mechanisms for attaching the incisor proportion gauge to the secondary removably attachable tool.

The slidable primary upper plate 50 can further include, when viewing from the right-side of the slidable primary upper plate 50, two right-side primary planar segments 390 with a right-side primary concavity 395 formed therebetween as shown in FIGS. 1 and 5 and as described herein. Similarly, there can be two left-side primary planar segments 380 with a left-side primary concavity 385 formed therebetween on the primary upper plate 50 when viewing from the left side thereof as depicted in FIGS. 1 and 5 and as described herein.

The slidable primary upper plate 50, as depicted in FIG. 1, can be removably attached to the second slot 45 of the primary removably attachable tool 10. According to this embodiment, the slidable primary upper plate 50 can be first placed on a primary top surface 160 of the primary removably attachable tool 10 with the primary threaded hole 55 of the slidable primary upper plate 50 aligned with the second slot 45. Then, a primary screw 60 (which can include a primary screw head 65, a slidable primary lower plate 70, and a primary threaded portion 75) can be placed on a primary bottom surface 165 of the primary removably attachable tool 10 with the primary threaded portion 75 of the primary screw 60 inserted into the second slot 45 and a portion of the primary threaded hole 55. After which, the primary screw head 65 can be turned clockwise to allow the primary threaded portion 75 to be fully or partially engaged with the primary threaded hole 55.

In a non-limiting embodiment, the primary screw head 65 can be turned clockwise so that the primary threaded portion 75 of the primary screw 60 can be located within the entire first thickness T1 of the slidable primary upper plate 50 (fully engaged with the primary threaded hole 55). Conversely, in another non-limiting embodiment, the primary screw head 65 can be turned clockwise so that the primary threaded portion 75 of the primary screw 60 can be located partially within the first thickness T1 of the slidable primary upper plate 50 (partially engaged with the primary threaded hole 55).

In an embodiment, the slidable primary lower plate 70 of the primary screw 60 can contact the primary bottom surface 165 of the primary removably attachable tool 10 as the primary screw head 65 is being turned clockwise and the threaded portion 75 is being screwed further into the primary threaded hole 55 of the slidable primary upper plate 50. In this regard, the ease of sliding the slidable primary upper plate 50 and the slidable primary lower plate 70 along the second slot 45 can be dictated by how far the primary threaded portion 75 is screwed into the primary threaded hole 55 of the slidable primary upper plate 50.

In an embodiment, the primary screw head 65 can be turned counterclockwise to lessen the engagement of the primary threaded portion 75 with the primary threaded hole 55 at any point of the engagement (i.e., fully engaged or partially engaged) as mentioned above or to fully withdraw the primary threaded portion 75 from the primary threaded hole 55.

The primary removably attachable tool 10 can further include at least one slidable pin. The at least one slidable pin can include at least two of a first slidable pin 80, a second slidable pin 85, a third slidable pin 90, a fourth slidable pin 95, and a fifth slidable pin 100 as shown in FIG. 1. In a further non-limiting embodiment, the at least one slidable pin can include all of the first slidable pin 80, the second slidable pin 85, the third slidable pin 90, the fourth slidable pin 95, and the fifth slidable pin 100. Each of the first slidable pin 80, the second slidable pin 85, the third slidable pin 90, the fourth slidable pin 95, and the fifth slidable pin 100 can be configured to be slidably positioned along various parts of a patient's face as described herein.

In an embodiment, the first slidable pin 80, the second slidable pin 85, the third slidable pin 90, and the fifth slidable pin 100 can be structurally the same. In this context, each of the first slidable pin 80, the second slidable pin 85, the third slidable pin 90, and the fifth slidable pin 100 can include a tertiary length L3 of about 37 mm. Each of the first slidable pin 80, the second slidable pin 85, the third slidable pin 90, and the fifth slidable pin 100 can include a first segment 105, a second segment 110, and a third segment 115 with a length of about 7 mm, about 15 mm, and about 15 mm, respectively, as illustrated in FIG. 1. Other lengths may be suitable herein.

The first segment 105, the second segment 110, and the third segment 115 of each of the first slidable pin 80, the second slidable pin 85, the third slidable pin 90, and the fifth slidable pin 100 can define a measuring pin assembly. In this context, the first segment 105, the second segment 110, and the third segment 115 of the measuring pin assembly can include a slidable primary top panel 120, a first converging portion 125, and a first pointer portion 130, respectively, as seen in FIG. 1. The first converging portion 125 can be connected to the slidable primary top panel 120 and the first pointer portion 130.

The slidable primary top panel 120 can include a secondary threaded hole 135 located therein as indicated in FIG. 1. Specifically, the secondary threaded hole 135 can extend the full thickness of the slidable primary top panel 120 with a terminal end on a primary bottom side 490 of the slidable primary top panel 120 as shown in FIG. 1. In this aspect, the secondary threaded hole 135 can allow a secondary threaded portion 150 to be rotatable therein. The secondary threaded portion 150 can be attached to a secondary screw head 140 which can be part of a secondary screw 145 as displayed in FIG. 1. The secondary screw head 140 can be located on a primary top side 495 of the slidable primary top panel 120.

In an embodiment, the slidable primary top panel 120 can be removably attached to the first slot 40 of the primary removably attachable tool 10 as depicted in FIG. 1. According to this particular example, the slidable primary top panel 120 can be first placed on the primary top surface 160 of the primary removably attachable tool 10 with the secondary threaded portion 150 of the secondary screw 145 aligned within the first slot 40. Then, a slidable secondary lower plate 155, which can include a threaded hole (not shown), can be placed on the primary bottom surface 165 of the primary removably attachable tool 10 with the secondary threaded portion 150 of the secondary screw 145 inserted into a portion of the threaded hole of the slidable secondary lower plate 155 while also being inserted into the first slot 40 as shown in FIG. 1. After which, the secondary screw head 140 can be turned clockwise to allow the secondary threaded portion 150 of the secondary screw 145 to be fully or partially engaged with the threaded hole of the slidable secondary lower plate 155.

In certain non-limiting embodiments, the secondary screw head 140 of the secondary screw 145 can be turned clockwise so that the secondary threaded portion 150 can be located within an entire second thickness T2 of the slidable secondary lower plate 155 (fully engaged with the threaded hole). Conversely, in a particular non-limiting embodiment, the secondary screw head 140 of the secondary screw 145 can be turned clockwise so that the secondary threaded portion 150 can be located partially within the second thickness T2 of the slidable secondary lower plate 155 (partially engaged with the threaded hole).

In an embodiment, the slidable secondary lower plate 155 can contact the primary bottom surface 165 of the primary removably attachable tool 10 as the secondary screw head 140 is being turned clockwise and the secondary threaded portion 150 is being screwed further into the threaded hole of the slidable secondary lower plate 155. In this aspect, the ease of sliding the slidable primary top panel 120 and the slidable secondary lower plate 155 along the first slot 40 can be dictated by how far the secondary threaded portion 150 is screwed into the threaded hole of the slidable secondary lower plate 155.

In an embodiment, the secondary screw head 140 can be turned counterclockwise to lessen the engagement of the secondary threaded portion 150 with the threaded hole of the slidable secondary lower plate 155 at any point of the engagement (i.e., fully engaged or partially engaged) as mentioned above or to fully withdraw the secondary threaded portion 150 from the threaded hole of the slidable secondary lower plate 155.

As illustrated in FIG. 1, the first converging portion 125 and the first pointer portion 130 can be located above the primary top surface 160 of the primary removably attachable tool 10. In this respect, the first converging portion 125 and the first pointer portion 130 can slide above the slidable primary upper plate 50 and the primary top surface 160 of the primary removably attachable tool 10 as the slidable primary top panel 120 and the slidable secondary lower plate 155 are sliding along the first slot 40.

The fourth slidable pin 95 can include a quaternary length L4 of about 50 mm. In this aspect, the fourth slidable pin 95 can be longer than the first slidable pin 80, the second slidable pin 85, the third slidable pin 90, and the fifth slidable pin 100 as depicted in FIG. 1. The fourth slidable pin 95 can include a first part 170, a second part 175, a third part 180, and a fourth part 185 as seen in FIG. 1. Each of the first part 170, the second part 175, the third part 180, and the fourth part 185 can have a length of about 8 mm, about 7 mm, about 15 mm, and about 20 mm, respectively. Other lengths may be suitable herein.

The first part 170, the second part 175, the third part 180, and the fourth part 185 can define another measuring pin assembly. In this regard, the first part 170, the second part 175, the third part 180, and the fourth part 185 of the another measuring pin assembly can include a rear slidable secondary top plate 190, a front slidable secondary top plate 195, a second converging portion 200, and a second pointer portion 205, respectively, as indicated in FIG. 1. The rear slidable secondary top plate 190, the front slidable secondary top plate 195, the second converging portion 200, and the second pointer portion 205 can be connected to each other.

The front slidable secondary top plate 195 can include a tertiary threaded hole 210 located therein as displayed in FIG. 1. Specifically, the tertiary threaded hole 210 can extend the full thickness of the front slidable secondary top plate 195 with a terminal end on a secondary bottom side 500 of the front slidable secondary top plate 195 as shown in FIG. 1. In this context, the tertiary threaded hole 210 can allow a tertiary threaded portion 225 to be rotatable therein. The tertiary threaded portion 225 can be attached to a tertiary screw head 215 which can be part of a tertiary screw 220 as depicted in FIG. 1. The tertiary screw head 215 can be located on a secondary top side 505 of the front slidable secondary top plate 195.

In an embodiment, the front slidable secondary top plate 195 can be removably attached to the first slot 40 of the primary removably attachable tool 10 as shown in FIG. 1. According to this embodiment, the front slidable secondary top plate 195 can be first placed on the primary top surface 160 of the primary removably attachable tool 10 with the tertiary threaded portion 225 of the tertiary screw 220 aligned within the first slot 40. Then, a slidable tertiary lower plate 230, which can include a threaded hole (not shown), can be placed on the primary bottom surface 165 of the primary removably attachable tool 10 with the tertiary threaded portion 225 of the tertiary screw 220 inserted into a portion of the threaded hole of the slidable tertiary lower plate 230 while also being inserted into the first slot 40 as illustrated in FIG. 1. After which, tertiary screw head 215 can be turned clockwise to allow the tertiary threaded portion 225 of the tertiary screw 220 to be fully or partially engaged with the threaded hole of slidable tertiary lower plate 230.

In some non-limiting embodiments, the tertiary screw head 215 of the tertiary screw 220 can be turned clockwise so that the tertiary threaded portion 225 can be located within an entire third thickness T3 of the slidable tertiary lower plate 230 (fully engaged with the threaded hole). Conversely, as a non-limiting example, the tertiary screw head 215 of the tertiary screw 220 can be turned clockwise so that the tertiary threaded portion 225 can be located partially within the third thickness T3 of the slidable tertiary lower plate 230 (partially engaged with the threaded hole).

In an embodiment, the slidable tertiary lower plate 230 can contact the primary bottom surface 165 of the primary removably attachable tool 10 as the tertiary screw head 215 is being turned clockwise and the tertiary threaded portion 225 is being screwed further into the threaded hole of the slidable tertiary lower plate 230. In this aspect, the ease of sliding the front slidable secondary top plate 195, the rear slidable secondary top plate 190, and the slidable tertiary lower plate 230 along the first slot 40 can be dictated by how far the tertiary threaded portion 225 is screwed into the threaded hole of the slidable tertiary lower plate 230.

In an embodiment, the tertiary screw head 215 can be turned counterclockwise to lessen the engagement of the tertiary threaded portion 225 with the threaded hole of the slidable tertiary lower plate 230 at any point of the engagement (i.e., fully engaged or partially engaged) as mentioned above or to fully withdraw the tertiary threaded portion 225 from the threaded hole of the slidable tertiary lower plate 230.

As seen in FIG. 1, the second converging portion 200 and the second pointer portion 205 can be located above the primary top surface 160 of the primary removably attachable tool 10. In this respect, the second converging portion 200 can slide above the slidable primary upper plate 50 and the primary top surface 160 of the primary removably attachable tool 10 as the front slidable secondary top plate 195, the rear slidable secondary top plate 190, and the slidable tertiary lower plate 230 are sliding along the first slot 40.

Figure 2:
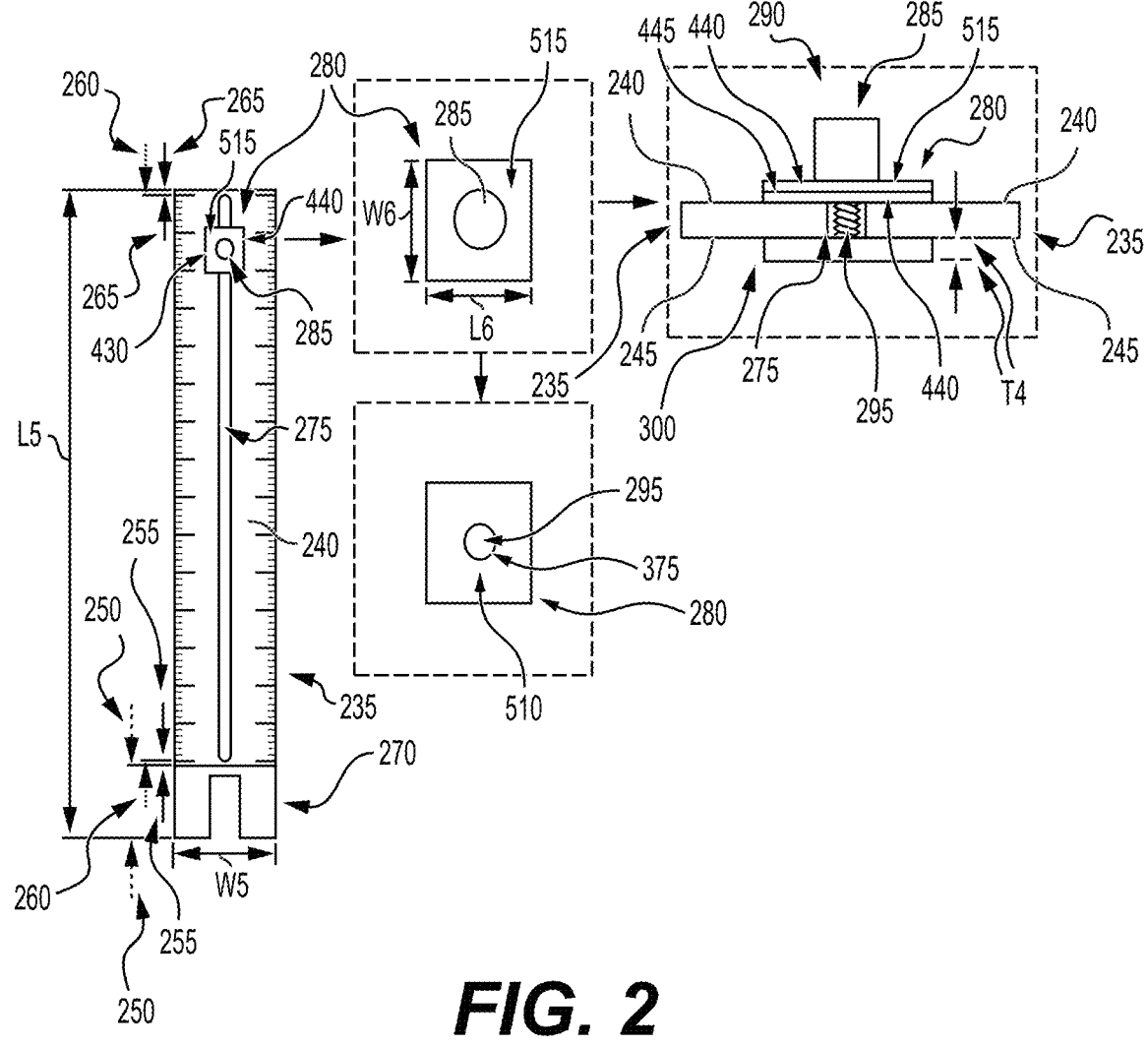
FIG. 2 depicts a secondary removably attachable tool with various components attached thereto.

FIG. 2 depicts a secondary removably attachable tool 235 which can also be part of the tool assembly 15 as shown in FIG. 6. The secondary removably attachable tool 235 can include a ruler with various markings representing numbers for measurement purposes. The secondary removably attachable tool 235 can include a secondary top surface 240 and a secondary bottom surface 245 as illustrated in FIG. 2. The secondary removably attachable tool 235 can also include a quinary length L5 of about 265 mm and a quinary width W5 of about 30 mm as seen in FIG. 2. Other lengths and widths may be suitable herein. The secondary removably attachable tool 235 can include a first section 250, a second section 255, a third section 260, and a fourth section 265 as indicated in FIG. 2.

Figure 4:
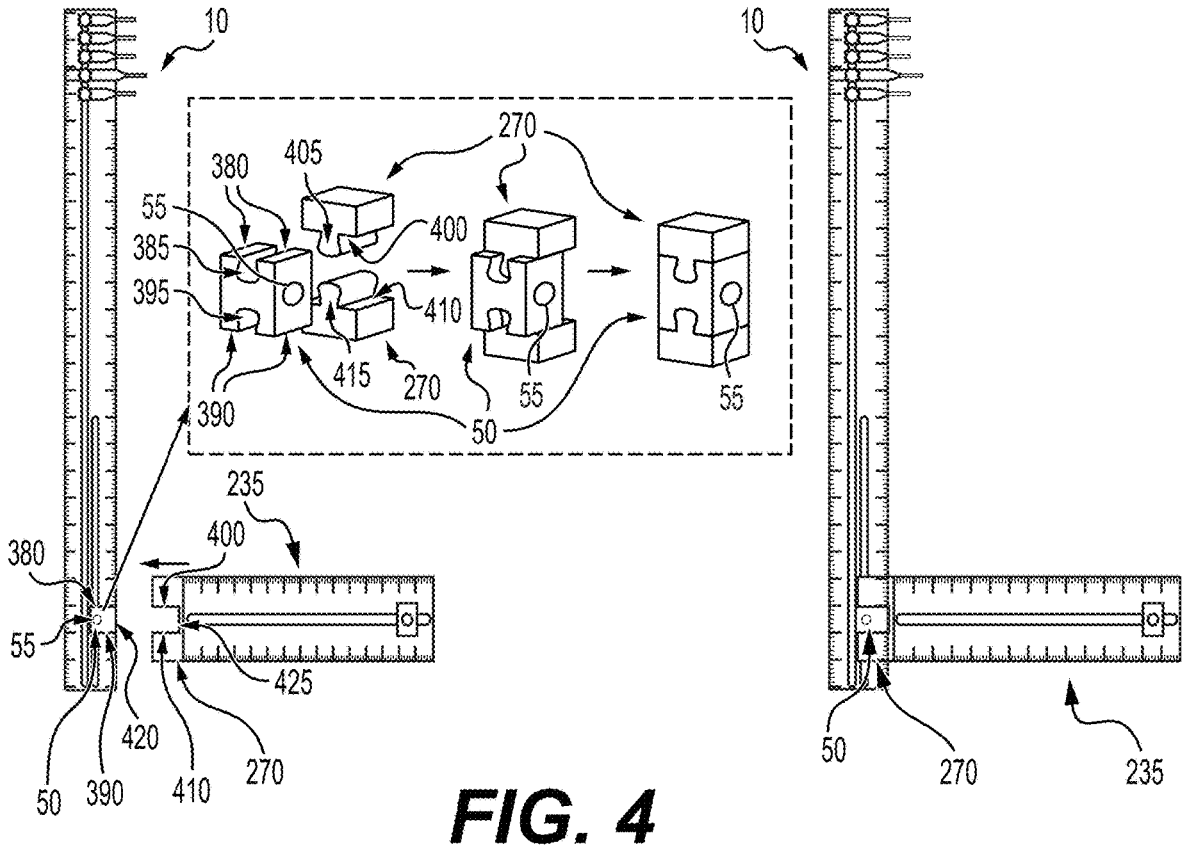
FIG. 4 depicts sliding attachment mechanisms for attaching the secondary removably attachable tool to the primary removably attachable tool.

As displayed in FIG. 2, the first section 250, which can have a length of about 15 mm, of the secondary removably attachable tool 235 can include a primary transparent recess component 270. Other lengths may be suitable herein. The primary transparent recess component 270 can be U-shaped. The transparency of the primary transparent recess component 270 can allow a user (e.g., clinician or any other user) to see the various markings (numbers) on the primary removably attachable tool 10 when the former is attached to the latter as depicted in FIGS. 4 and 6 and as described herein.

The secondary removably attachable tool 235, as depicted in FIG. 2, can include a third slot 275. In an embodiment, an entire third length of the third slot 275 can extend within the third section 260 of the secondary removably attachable tool 235. The third slot 275 can be perpendicular to the first slot 40 and the second slot 45 when the secondary removably attachable tool 235 is removably attached to the primary removably attachable tool 10 as depicted in FIG. 6.

The secondary removably attachable tool 235 can further include a slidable secondary upper plate 280 as shown in FIG. 2. The slidable secondary upper plate 280 can include a senary length L6 and a senary width W6 of about 11 mm. Other lengths and widths may be suitable herein. The slidable secondary upper plate 280 can include a quaternary threaded hole 375 located therein as shown in FIG. 2. Specifically, the quaternary threaded hole 375 can extend the full thickness of the slidable secondary upper plate 280 with a terminal end on a tertiary bottom side 510 of the slidable secondary upper plate 280. In this regard, the quaternary threaded hole 375 can allow a quaternary threaded portion 295 to be rotatable therein. The quaternary threaded portion 295 can be attached to a quaternary screw head 285 which can be part of a quaternary screw 290 as illustrated in FIG. 2. The quaternary screw head 285 can be located on a tertiary top side 515 of the slidable secondary upper plate 280.

The slidable secondary upper plate 280 can further include, when viewing from the front side of the slidable secondary upper plate 280, two front-side secondary planar segments 440 with a front-side secondary concavity 445 formed therebetween as shown in FIGS. 2 and 5 and as described herein. Similarly, there can be two rear-side secondary planar segments 430 with a rear-side secondary concavity 435 formed therebetween as shown in FIGS. 2 and 5 and described herein.

The slidable secondary upper plate 280, as seen in FIG. 2, can be removably attached to the third slot 275 of the secondary removably attachable tool 235. Corresponding to this embodiment, the slidable secondary upper plate 280 can be first placed on the secondary top surface 240 of the secondary removably attachable tool 235 with the quaternary threaded portion 295 of the quaternary screw 290 aligned within the third slot 275. Then, a slidable quaternary lower plate 300, which can include a threaded hole (not shown), can be placed on the secondary bottom surface 245 of the secondary removably attachable tool 235 with the quaternary threaded portion 295 of the quaternary screw 290 inserted into a portion of the threaded hole of the slidable quaternary lower plate 300 while also being inserted into the third slot 275 as indicated in FIG. 2. After which, the quaternary screw head 285 can be turned clockwise to allow the quaternary threaded portion 295 of the quaternary screw 290 to be fully or partially engaged with the threaded hole of the slidable quaternary lower plate 300.

In a non-limiting embodiment, the quaternary screw head 285 of the quaternary screw 290 can be turned clockwise so that the quaternary threaded portion 295 can be located within an entire fourth thickness T4 of the slidable quaternary lower plate 300 (fully engaged with the threaded hole). Conversely, in another non-limiting embodiment, the quaternary screw head 285 of the quaternary screw 290 can be turned clockwise so that the quaternary threaded portion 295 can be located partially within the fourth thickness T4 of the slidable quaternary lower plate 300 (partially engaged with the threaded hole).

In an embodiment, the slidable quaternary lower plate 300 can contact the secondary bottom surface 245 of the of the secondary removably attachable tool 235 as the quaternary screw head 285 is being turned clockwise and the quaternary threaded portion 295 is being screwed further into the threaded hole of the slidable quaternary lower plate 300. In this context, the ease of sliding the slidable secondary upper plate 280 and the slidable quaternary lower plate 300 along the third slot 275 can be dictated by how far the quaternary threaded portion 295 is screwed into the threaded hole of the slidable quaternary lower plate 300.

In an embodiment, the quaternary screw head 285 can be turned counterclockwise to lessen the engagement of the quaternary threaded portion 295 with the threaded hole of the slidable quaternary lower plate 300 at any point of the engagement (i.e., fully engaged or partially engaged) as mentioned above or to fully withdraw the quaternary threaded portion 295 from the threaded hole of the slidable quaternary lower plate 300.

Figure 3:
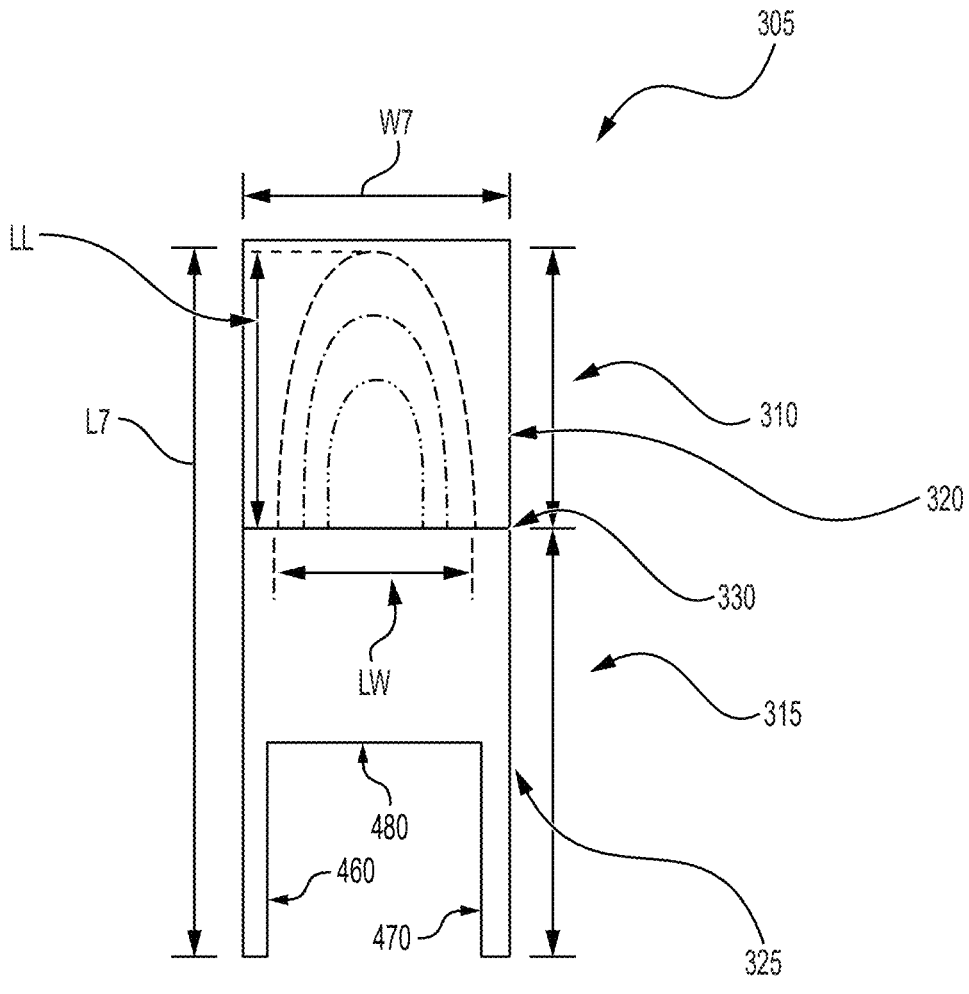
FIG. 3 depicts an incisor proportion gauge.

FIG. 3 depicts a gauge 305 which can also be part of the tool assembly 15 as shown in FIG. 6. The gauge 305 can be an incisor proportion gauge 305. The incisor proportion gauge 305 can include a first partition 310 and a second partition 315 with a length of about 16 mm and about 24 mm, respectively, as illustrated in FIG. 3. The total length of the incisor proportion gauge 305, which is a septenary length L7, is the combined lengths of the first partition 310 and the second partition 315 which is about 40 mm. The incisor proportion gauge 305 can also include a septenary width W7 of about 15 mm. Other lengths and widths may be suitable herein.

The first partition 310 and the second partition 315 of the incisor proportion gauge 305 can include an incisor proportion gauge head 320 and a secondary transparent recess component 325, respectively, as seen in FIG. 3. The secondary transparent recess component 325 can be U-shaped. The secondary transparent recess component 325 can also include two front-side secondary planar portions 470 with a front-side secondary protrusion 475 formed therebetween and two rear-side secondary planar portions 460 with a rear-side secondary protrusion 465 formed therebetween as shown in FIGS. 3 and 5. The secondary transparent recess component 325 can further include a secondary planar part 480 as displayed in FIGS. 3 and 5. The transparency of the secondary transparent recess component 325 can allow the user to see the various markings (numbers) on the secondary removably attachable tool 235 when the former is attached to the latter as indicated in FIG. 6 and described herein. Between the incisor proportion gauge head 320 and the secondary transparent recess component 325 is an incisal edge indicator line 330.

Figure 12:
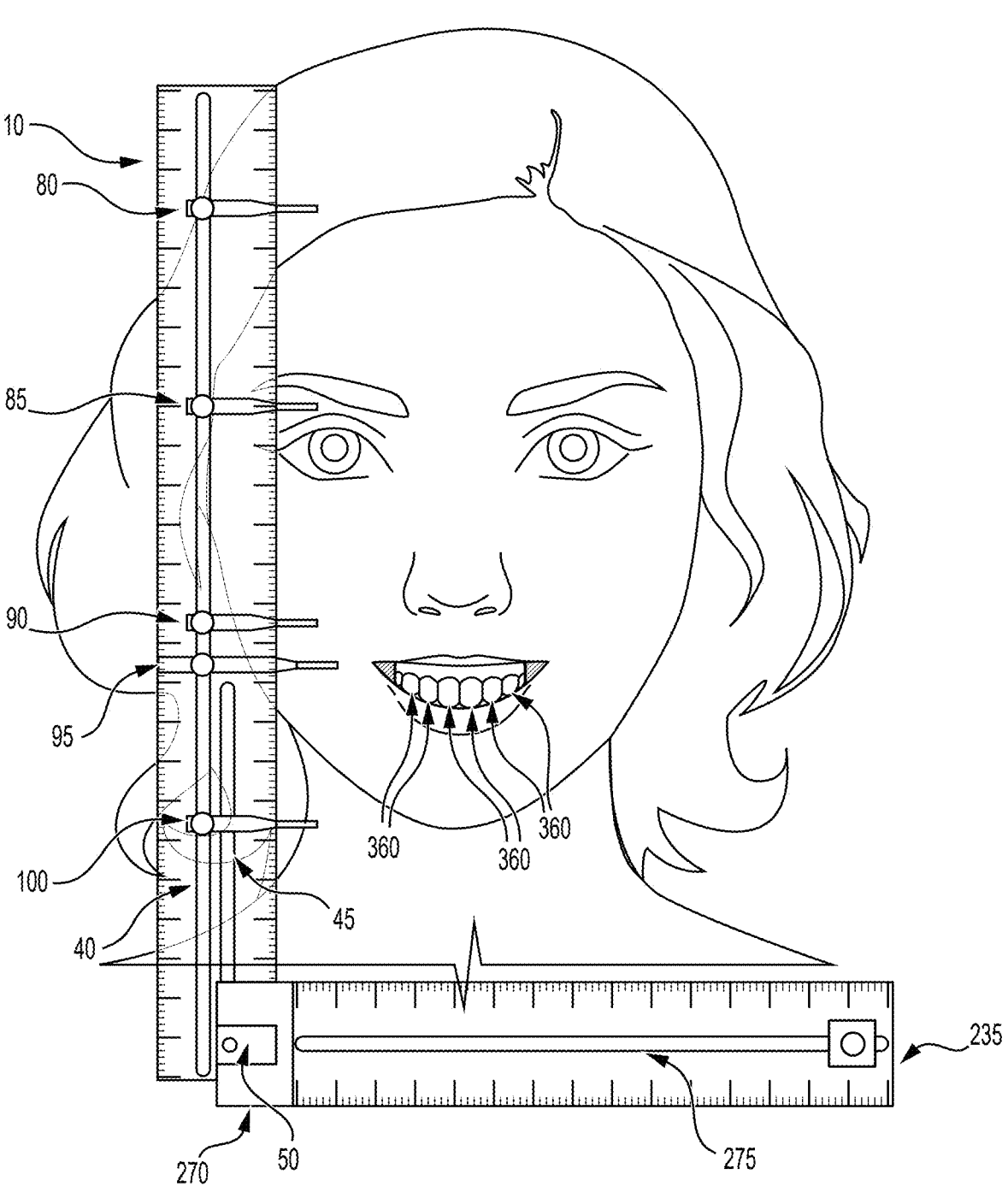
FIG. 12 depicts attaching the secondary removably attachable tool to the primary removably attachable tool.

The incisor proportion gauge head 320 can include three color-coded lines comprising a blue color, a green color, and a red color as displayed in FIG. 3. Each of the blue color, the green color, and the red color can have a line width LW of about 8 mm, about 10.5 mm, and about 13 mm, respectively, and a line length LL of about 10 mm, about 12.5 mm, and about 15.5 mm, respectively. The mentioned line width LW and the line length LL of each of the blue color, the green color, and the red color correspond to standard incisal proportions and can be adjusted to such proportions accordingly. The incisor proportion gauge head 320 can be transparent in order for the user to assess the proportions of the maxillary anterior teeth 360 as shown in FIG. 12 and described herein.

As discussed supra, the primary transparent recess component 270 of the secondary removably attachable tool 235 can be removably attached to the primary removably attachable tool 10 via the slidable primary upper plate 50 as shown in FIGS. 4 and 6. To accomplish this, the primary transparent recess component 270 can include two right-side primary planar portions 410 with a right-side primary protrusion 415 formed therebetween as shown in FIG. 4. Similarly, there can be two left-side primary planar portions 400 with a left-side primary protrusion 405 formed therebetween as shown in FIG. 4.

According to these configurations, when the primary transparent recess component 270 is pushed towards the slidable primary upper plate 50, the two right-side primary planar portions 410 and the right-side primary protrusion 415 of the primary transparent recess component 270 can slidably engage with the two right-side primary planar segments 390 and the right-side primary concavity 395, respectively, of the slidable primary upper plate 50 as shown in FIG. 4. Simultaneously, the two left-side primary planar portions 400 and the left-side primary protrusion 405 of the primary transparent recess component 270 can slidably engage with the two left-side primary planar segments 380 and the left-side primary concavity 385, respectively, of the slidable primary upper plate 50 as shown in FIG. 4. Once the right-side primary protrusion 415 and the left-side primary protrusion 405 are fully engaged with the right-side primary concavity 395 and the left-side primary concavity 385, the primary planar part 425 of the transparent recess component 270 can contact the front planar segment 420 of the slidable primary upper plate 50 as shown in FIG. 4. According to this embodiment, the secondary removably attachable tool 235 can be removably attached and secured to the primary removably attachable tool 10.

As described above, the secondary transparent recess component 325 of the incisor proportion gauge 305 can be removably attached to the secondary removably attachable tool 235 via the slidable secondary upper plate 280 as shown in FIGS. 5-6. To accomplish this, the slidable secondary upper plate 280 can include two front-side secondary planar segments 440 with a front-side secondary concavity 445 formed therebetween and two rear-side secondary planar segments 430 with a rear-side secondary concavity 435 formed therebetween as displayed in FIG. 5. The slidable secondary upper plate 280 can further include two right-side secondary planar segments 450 with a right-side secondary concavity (not shown but the right-side secondary concavity have the same concavity shape as the rear-side secondary concavity 435 and the front-side secondary concavity 445) formed therebetween and two left-side secondary planar segments 455 with a left-side secondary concavity (not shown but the left-side secondary concavity have the same concavity shape as the rear-side secondary concavity 435 and the front-side secondary concavity 445) formed therebetween as shown in FIG. 5.

As described supra, the secondary transparent recess component 325 can include two front-side secondary planar portions 470 with a front-side secondary protrusion 475 formed therebetween and two rear-side secondary planar portions 460 with a rear-side secondary protrusion 465 formed therebetween as shown in FIG. 5.

Figure 7:
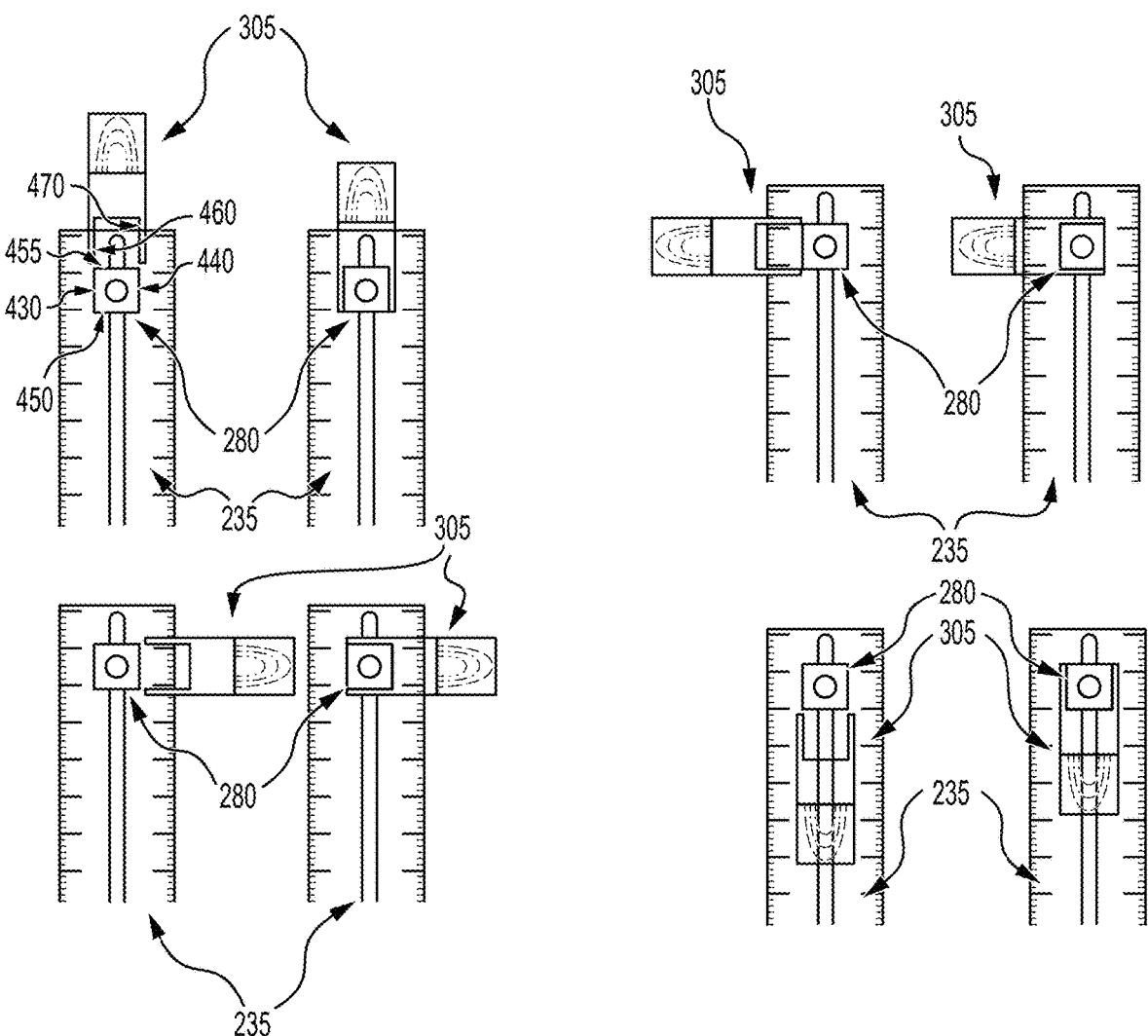
FIG. 7 depicts the various orientations of the incisor proportion gauge on the secondary removably attachable tool.

According to these configurations and in a non-limiting embodiment, when the secondary transparent recess component 325 is pushed towards the slidable secondary upper plate 280, the two front-side secondary planar portions 470 and the front-side secondary protrusion 475 of the secondary transparent recess component 325 can slidably engage with the two front-side secondary planar segments 440 and the front-side secondary concavity 445, respectively, of the slidable secondary upper plate 280 as shown in FIG. 5. Simultaneously, the two rear-side secondary planar portions 460 and the rear-side secondary protrusion 465 of the secondary transparent recess component 325 can slidably engage with the two rear-side secondary planar segments 430 and the rear-side secondary concavity 435, respectively, of the slidable secondary upper plate 280 as shown in FIG. 5. Once the front-side secondary protrusion 475 and the rear-side secondary protrusion 465 are fully engaged with the front-side secondary concavity 445 and the rear-side secondary concavity 435, respectively, the secondary planar part 480 of the secondary transparent recess component 325 can contact the two left-side secondary planar segments 455 of the slidable secondary upper plate 280 as shown in FIGS. 5 and 7. According to this embodiment, the incisor proportion gauge 305 can be removably attached and secured to the secondary removably attachable tool 235, and the incisor proportion gauge 305 can be oriented rightward with respect to the secondary removably attachable tool 235 during the removably attaching and securing step of the secondary removably attachable tool 235 and the primary removably attachable tool 10 as discussed supra.

Similarly, and according to another non-limiting embodiment, the two front-side secondary planar portions 470 and the front-side secondary protrusion 475 of the secondary transparent recess component 325 can slidably engage with the two right-side secondary planar segments 450 and the right-side secondary concavity, respectively, of the slidable secondary upper plate 280 as shown in FIG. 7. Simultaneously, the two rear-side secondary planar portions 460 and the rear-side secondary protrusion 465 of the secondary transparent recess component 325 can slidably engage with the two left-side secondary planar segments 455 and the left-side secondary concavity, respectively, of the slidable secondary upper plate 280 as shown in FIG. 7. Once the front-side secondary protrusion 475 and the rear-side secondary protrusion 465 are fully engaged with the right-side secondary concavity and the left-side secondary concavity, respectively, the secondary planar part 480 of the secondary transparent recess component 325 can contact the two front-side secondary planar segments 440 of the slidable secondary upper plate 280 as shown in FIG. 7. According to this embodiment, the incisor proportion gauge 305 can be removably attached and secured to the secondary removably attachable tool 235, and the incisor proportion gauge 305 can be oriented downward with respect to the secondary removably attachable tool 235 during the removably attaching and securing step of the secondary removably attachable tool 235 and the primary removably attachable tool 10 as mentioned previously.

According to a further non-limiting embodiment, the two front-side secondary planar portions 470 and the front-side secondary protrusion 475 of the secondary transparent recess component 325 can slidably engage with the two rear-side secondary planar segments 430 and the rear-side secondary concavity, respectively, of the slidable secondary upper plate 280 as shown in FIG. 7. Simultaneously, the two rear-side secondary planar portions 460 and the rear-side secondary protrusion 465 of the secondary transparent recess component 325 can slidably engage with the two front-side secondary planar segments 440 and the front-side secondary concavity, respectively, of the slidable secondary upper plate 280 as shown in FIG. 7. Once the front-side secondary protrusion 475 and the rear-side secondary protrusion 465 are fully engaged with the rear-side secondary concavity and the front-side secondary concavity, respectively, the secondary planar part 480 of the secondary transparent recess component 325 can contact the two right-side secondary planar segments 450 of the slidable secondary upper plate 280 as shown in FIG. 7. According to this embodiment, the incisor proportion gauge 305 can be removably attached and secured to the secondary removably attachable tool 235, and the incisor proportion gauge 305 can be oriented leftward with respect to the secondary removably attachable tool 235 during the removably attaching and securing step of the secondary removably attachable tool 235 and the primary removably attachable tool 10 as described supra.

According to a particular non-limiting embodiment, the two front-side secondary planar portions 470 and the front-side secondary protrusion 475 of the secondary transparent recess component 325 can slidably engage with the two left-side secondary planar segments 455 and the left-side secondary concavity, respectively, of the slidable secondary upper plate 280 as shown in FIG. 7. Simultaneously, the two rear-side secondary planar portions 460 and the rear-side secondary protrusion 465 of the secondary transparent recess component 325 can slidably engage with the two right-side secondary planar segments 450 and the right-side secondary concavity, respectively, of the slidable secondary upper plate 280 as shown in FIG. 7. Once the front-side secondary protrusion 475 and the rear-side secondary protrusion 465 are fully engaged with the left-side secondary concavity and the right-side secondary concavity, respectively, the secondary planar part 480 of the secondary transparent recess component 325 can contact the two rear-side secondary planar segments 430 of the slidable secondary upper plate 280 as shown in FIG. 7. According to this embodiment, the incisor proportion gauge 305 can be removably attached and secured to the secondary removably attachable tool 235, and the incisor proportion gauge 305 can be oriented upward with respect to the secondary removably attachable tool 235 during the removably attaching and securing step of the secondary removably attachable tool 235 and the primary removably attachable tool 10 as described herein.

As described supra, the secondary removably attachable tool 235 can be removably attached to the primary removably attachable tool 10 by inserting the primary transparent recess component 270 of the secondary removably attachable tool 235 between the primary top surface 160 of the primary removably attachable tool 10 and the slidable primary upper plate 50 as depicted in FIG. 6. Then, the primary screw head 65, as shown in FIG. 1, can be turned clockwise to secure the primary transparent recess component 270 to the slidable primary upper plate 50 and the primary removably attachable tool 10 to form part of the tool assembly 15 as illustrated in FIG. 6. According to this particular example, after the securing step, the secondary removably attachable tool 235 can be configured to slide along the second slot 45 as described herein.

Likewise, the incisor proportion gauge 305 can be removably attached to the secondary removably attachable tool 235 by inserting the secondary transparent recess component 325 of the incisor proportion gauge 305 between the secondary top surface 240 of the secondary removably attachable tool 235 and the slidable secondary upper plate 280 as illustrated in FIG. 6. After which, the quaternary screw head 285, as seen in FIG. 2, can be turned clockwise to secure the secondary transparent recess component 325 to the slidable secondary upper plate 280 and the secondary removably attachable tool 235 to form the other part of the tool assembly 15 as indicated in FIGS. 5-6. According to this embodiment, after the securing step, the incisor proportion gauge 305 can be configured to slide along the third slot 275 as described herein. It should be noted that the attachment of the secondary removably attachable tool 235 to the primary removably attachable tool 10 and the attachment of the incisor proportion gauge 305 to the secondary removably attachable tool 235 can occur in any order without departing from the present subject matter.

Figure 8:
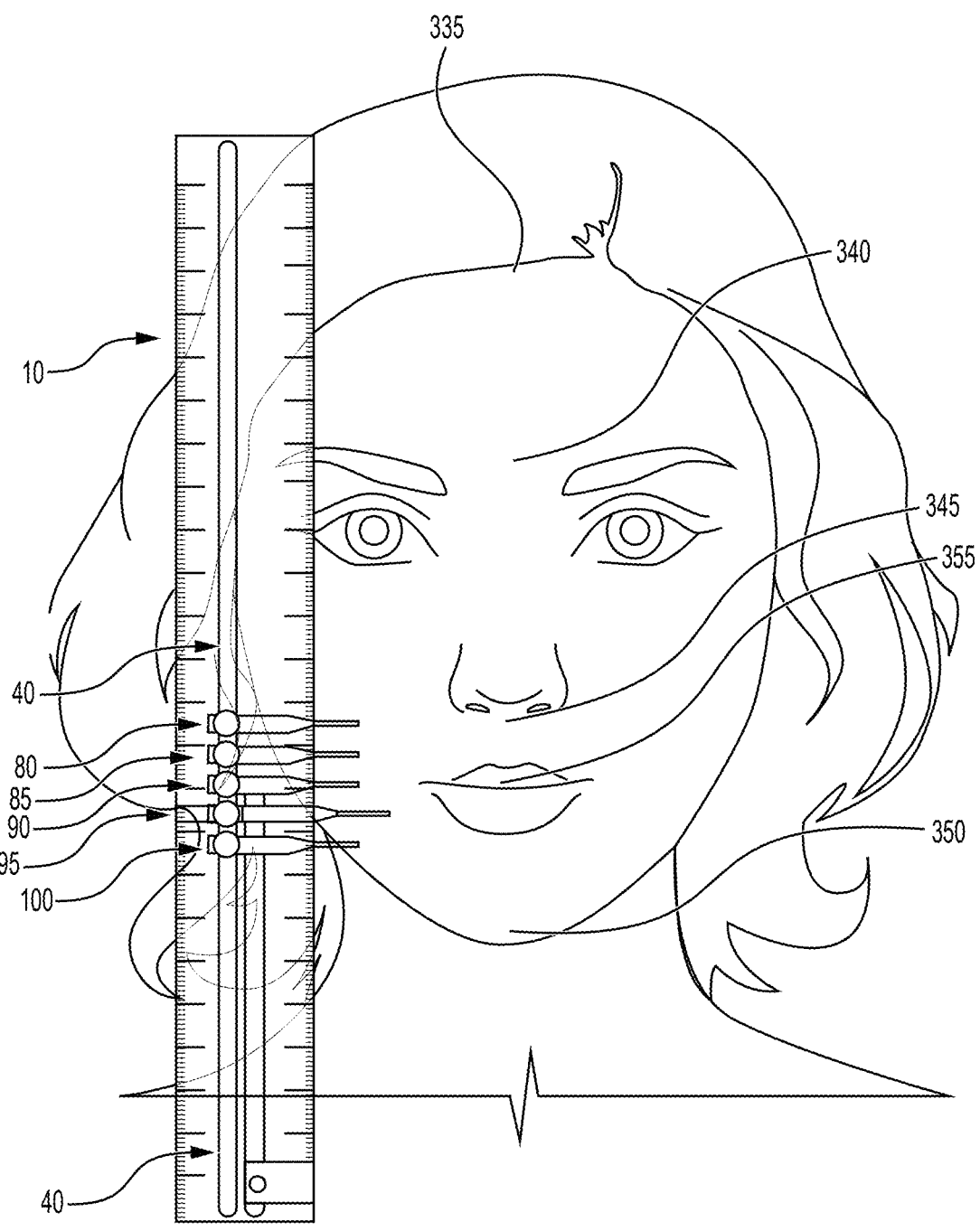
FIG. 8 depicts the primary removably attachable tool positioned in front of a patient's face.

In an embodiment, the present subject matter relates to a method of using the above tool assembly 15 to measure at least one facial feature of a patient as depicted in FIGS. 8-15. The method can include obtaining at least two slidable pins. The at least two slidable pins can include the first slidable pin 80, the second slidable pin 85, the third slidable pin 90, the fourth slidable pin 95, and the fifth slidable pin 100 as shown in FIG. 8. Each of the first slidable pin 80, the second slidable pin 85, the third slidable pin 90, the fourth slidable pin 95, and the fifth slidable pin 100 can be removably attached to the first slot 40 of the primary removably attachable tool 10 as described supra.

Next, the user can place the primary removably attachable tool 10 parallel and vertically in front of the patient's face as shown in FIG. 8 (Step 1). As illustrated in FIG. 8, anatomical facial landmarks of the patient's face can include a trichion point 335, glabella point 340, a subnasale point 345, a menton point 350, and an upper lip line 355. Anatomical facial landmarks of the maxillary anterior teeth 360 can be seen on FIG. 12.

Figure 9:
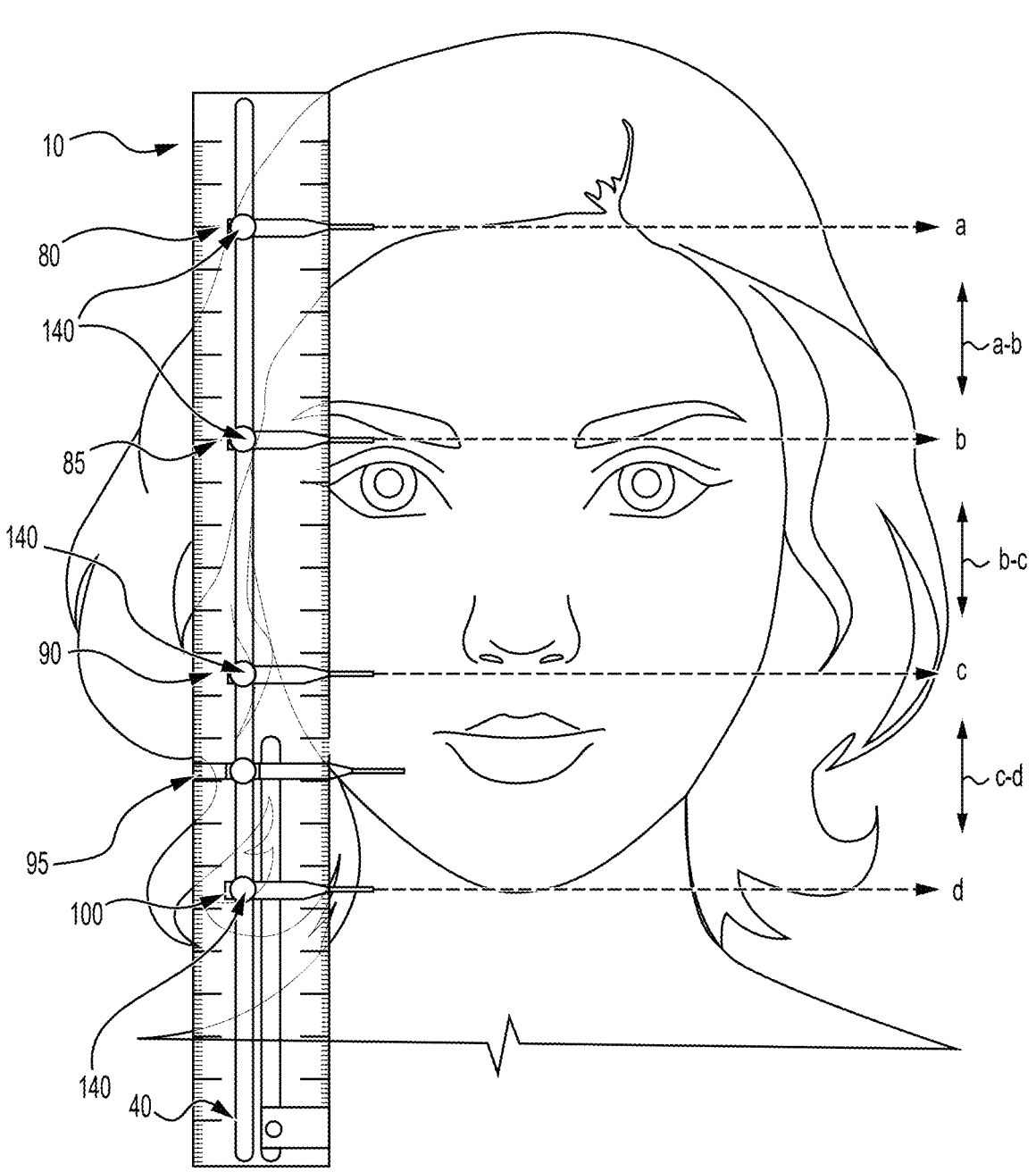
FIG. 9 depicts sliding a first slidable pin, a second slidable pin, a third slidable pin, and a fifth slidable pin towards various positions of the patient's face.

After placing the primary removably attachable tool 10 in front of the patient's face, the user can consecutively or sequentially slide the first slidable pin 80 and the second slidable pin 85 along the first slot 40 toward the trichion point 335 (corresponds to point a in FIG. 9) and the glabella point 340 (corresponds to point b in FIG. 9), respectively, as seen in FIG. 9 (Step 2). Once at the locations on the primary removably attachable tool 10 corresponding to the trichion point 335 and the glabella point 340, the first slidable pin 80 and the second slidable pin 85, respectively, can be secured to their respective locations via turning the secondary screw head 140 clockwise (Step 2). Next, the user can measure at least one facial feature of the patient based on a height difference between point a and point b (the height difference corresponds to a height difference between the first slidable pin 80 and the second slidable pin 85) (Step 3). Corresponding to this embodiment, the height difference between point a and point b corresponds to an upper facial height of the patient as seen in FIG. 9 (Step 3).

Afterwards, the user can slide the third slidable pin 90 along the first slot 40 towards the subnasale point 345 (corresponds to point c in FIG. 9) as indicated in FIG. 9 (Step 4). Once at the location on the primary removably attachable tool 10 corresponding to the subnasale point 345, the third slidable pin 90 can be secured to its location via turning the secondary screw head 140 clockwise (Step 4). Thereafter, the user can measure another of the at least one facial feature of the patient based on a height difference between point b and point c (the height difference corresponds to a height difference between the second slidable pin 85 and the third slidable pin 90) (Step 5). In this particular example, the height difference between point b and point c corresponds to the middle facial height of the patient as seen in FIG. 9 (Step 5).

Subsequently, the user can slide the fifth slidable pin 100 along the first slot 40 towards the menton point 350 (corresponds to point d in FIG. 9) as indicated in FIG. 9 (Step 6). Once at the location on the primary removably attachable tool 10 corresponding to the menton point 350, the fifth slidable pin 100 can be secured to its location via turning the secondary screw head 140 clockwise (Step 6). Following, the user can measure an additional of the at least one facial feature of the patient based on a height difference between point c and point d (the height difference corresponds to a height difference between the third slidable pin 90 and the fifth slidable pin 100) (Step 7). According to this embodiment, the height difference between point c and point d corresponds to the lower facial height of the patient as displayed in FIG. 9 (Step 7). Based on the height differences for the upper facial height (see Step 3), the middle facial height (see Step 5), and the lower facial height (see Step 7), the user can evaluate facial symmetry and identify any disproportion that may affect aesthetic or functional outcomes.

Figure 10:
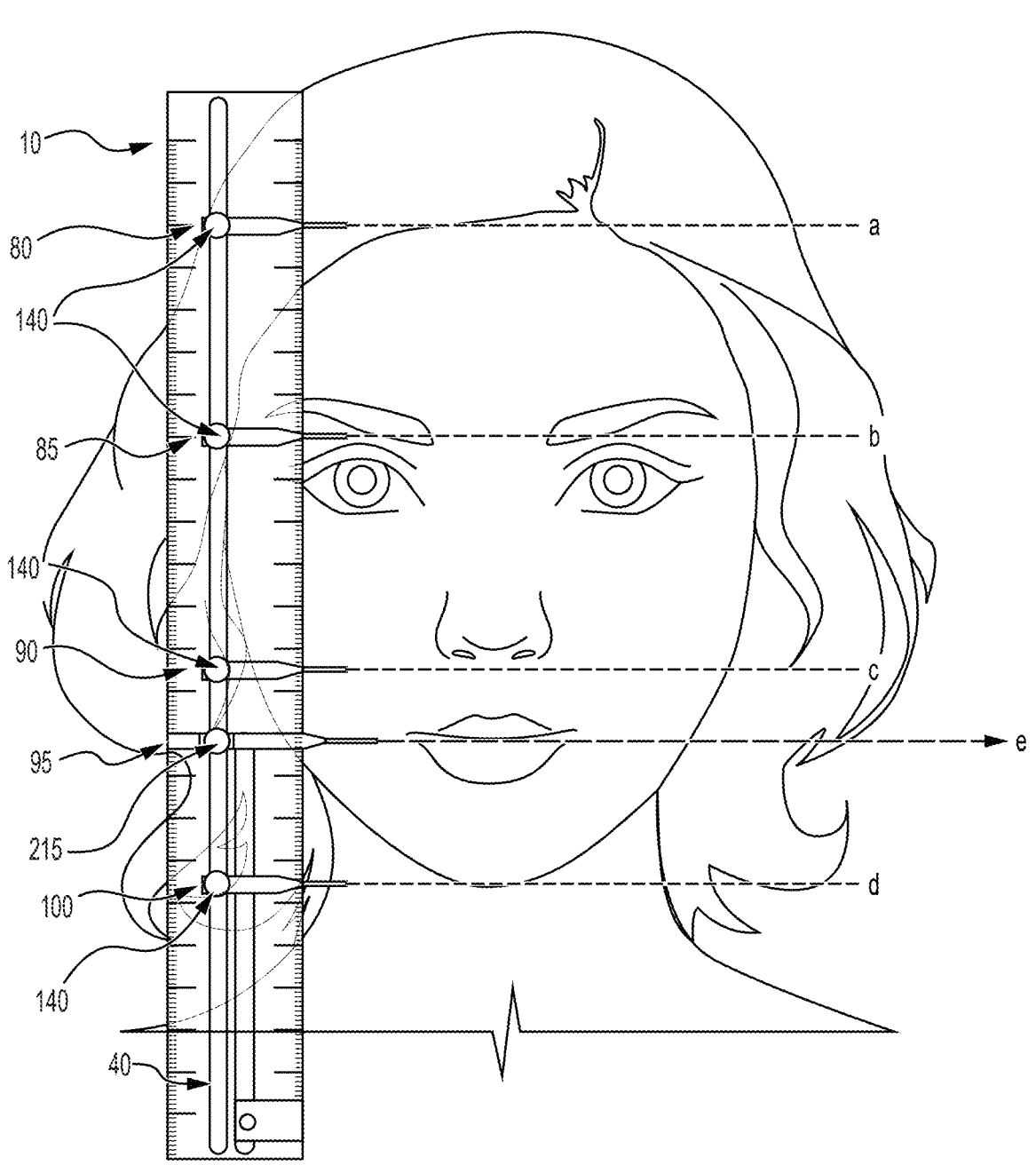
FIG. 10 depicts sliding a fourth slidable pin towards a first position of the upper lip line of the patient's face.

Successively, the user can slide the fourth slidable pin 95 along the first slot 40 towards a first position of the upper lip line 355 (corresponds to point e in FIG. 10) while the patient's mouth is at rest as indicated in FIG. 10 (Step 8). Once at the location on the primary removably attachable tool 10 corresponding to the first position of the upper lip line 355, the fourth slidable pin 95 can be secured to its location via turning the tertiary screw head 215 clockwise (Step 8). At this point, the user can record a first marking (number) on the ruler of the primary removably attachable tool 10 corresponding to the upper lip line 355 of the patient's mouth is resting (Step 9).

Figure 11:
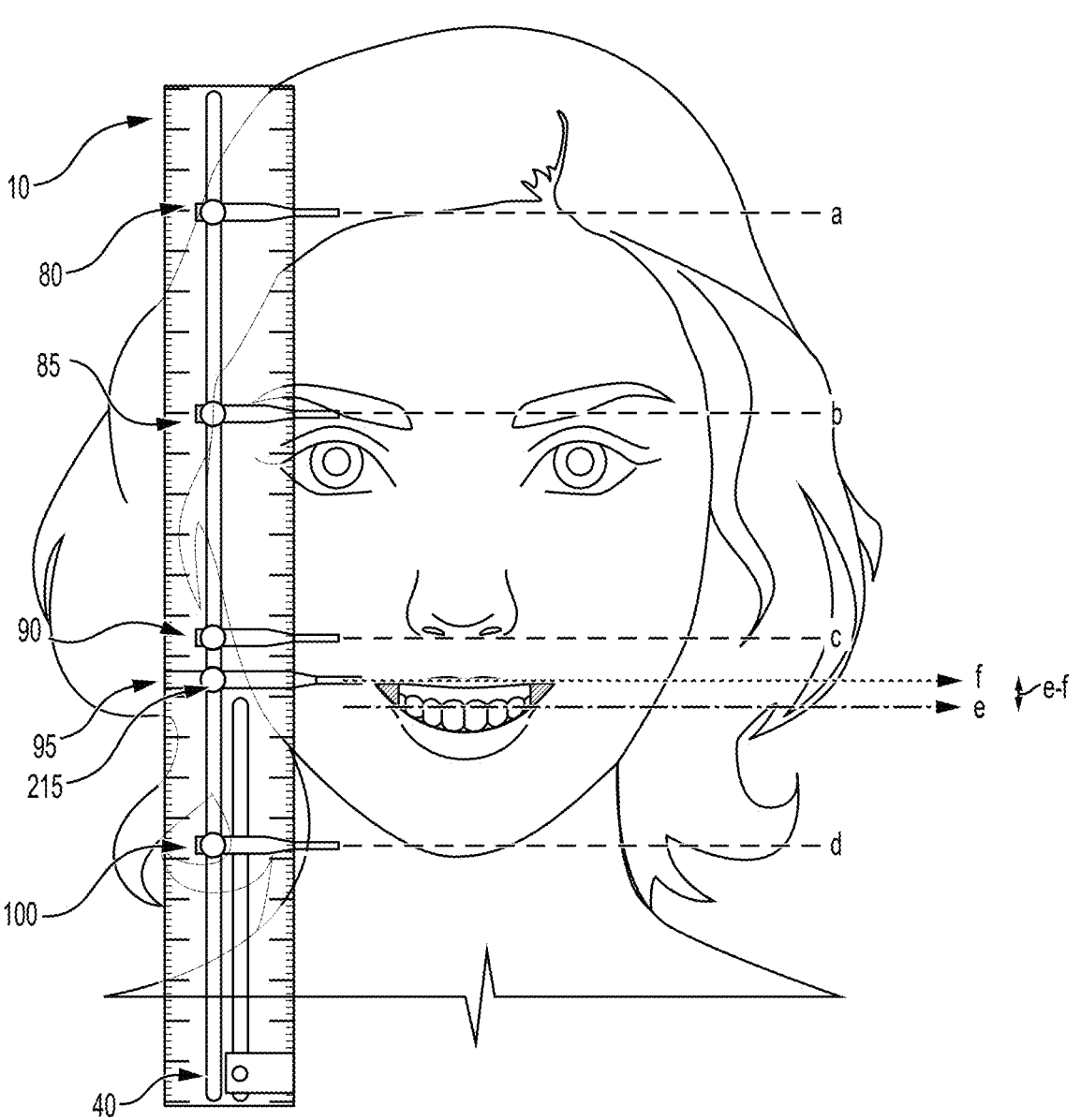
FIG. 11 depicts sliding the fourth slidable pin towards a second position of the upper lip line of the patient's face.

Then, the user can unsecure the fourth slidable pin 95 at its location corresponding to the first position via turning the tertiary screw head 215 counterclockwise and sliding the fourth slidable pin 95 along the first slot 40 towards a second position of the upper lip line 355 (corresponds to point f in FIG. 11) while the patient is smiling or after the patient has smiled as depicted in FIG. 11 (Step 10). Once at the location on the primary removably attachable tool 10 corresponding to the second position of the upper lip line 355, the fourth slidable pin 95 can be secured to its location via turning the tertiary screw head 215 clockwise (Step 10). After which, the user can record a second marking (number) on the ruler of the primary removably attachable tool 10 corresponding to the upper lip line 355 of the patient while the patient is smiling or after the patient has smiled (Step 11).

Next, the user can measure further at least one facial feature of the patient based on a height difference between point f and point e (the height difference corresponds to a height difference between the second marking and the first marking on the ruler) (Step 12). Corresponding to this embodiment, the height difference between point f and point e corresponds to an upper lip mobility as shown in FIG. 11 (Step 12). Based on the height difference of the upper lip mobility, the user can quantify the extent of upper lip movement during smiling, which is an important parameter in both aesthetic diagnosis and surgical planning.

Afterwards, the user can removably attach the secondary removably attachable tool 235 to the primary removably attachable tool 10 via the primary transparent recess component 270 and the slidable primary upper plate 50 as described previously (Step 13). Once attached and while the patient is still smiling, the secondary removably attachable tool 235 can slide along the second slot 45 towards the second position of the upper lip line 355 (corresponds to point f in FIG. 11 at Step 10) (Step 14). According to this embodiment, the slidable primary upper plate 50, the primary transparent recess component 270, and a portion of the secondary removably attachable tool 235 can slide beneath at least the fifth slidable pin 100 as the secondary removably attachable tool 235 slides along the second slot 45 towards the second position of the upper lip line 355 (Step 14). Once at the location on the primary removably attachable tool 10 corresponding to the second position of the upper lip line 355, the secondary removably attachable tool 235 can be secured to its location via turning the primary screw head 65 of the primary screw 60 (see FIG. 1) clockwise (Step 14). At this position, the secondary removably attachable tool 235 can be slightly below or adjacent to the fourth slidable pin 95, the left buccal (black) corridor 365, and the right buccal (black) corridor 370 as illustrated in FIG. 13 (Step 14).

Figure 13:
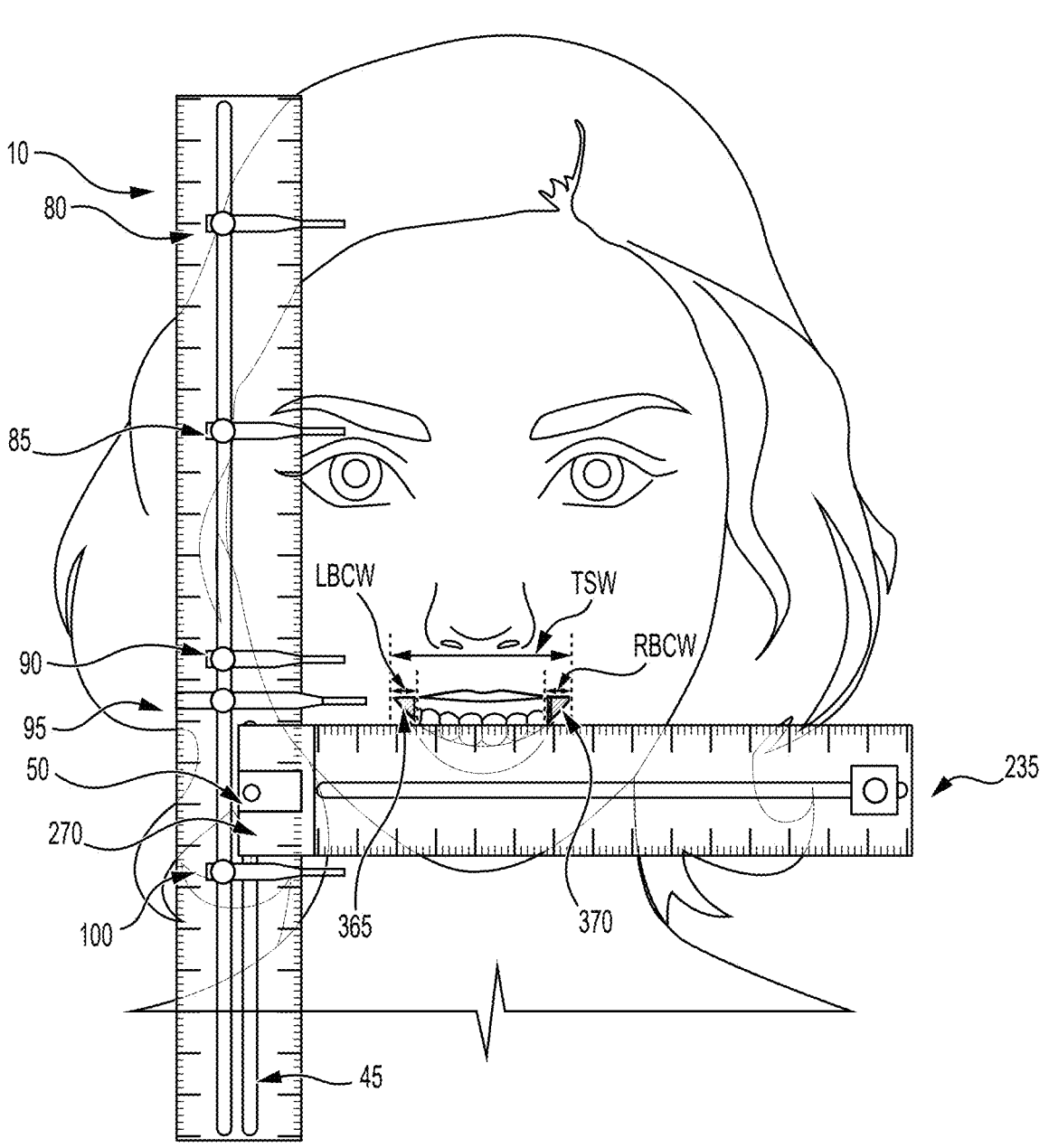
FIG. 13 depicts measuring a total smile width TSW, a left buccal corridor width LBCW, and a right buccal corridor width RBCW.

Thereafter, the user can record a third marking (number) and a fourth marking (number) on the ruler of the secondary removably attachable tool 235 corresponding to the far-left side of the left buccal (black) corridor 365 and the far-right side of the right buccal (black) corridor 370, respectively, while the patient is still smiling as seen in FIG. 13 (Step 15). Subsequently, the user can measure the total smile width (facial feature) TSW of the patient based on a difference between the third marking and the fourth marking on the ruler of the secondary removably attachable tool 235 (Step 16).

Following, the user can record a fifth marking (number) on the ruler of the secondary removably attachable tool 235 corresponding to the far-right side of the left buccal (black) corridor 365 while the patient is still smiling as indicated in FIG. 13 (Step 17). Likewise, the user can record a sixth marking (number) on the ruler of the secondary removably attachable tool 235 corresponding to the far-left side of the right buccal (black) corridor 370 while the patient is still smiling as displayed in FIG. 13 (Step 18). Following, the user can measure the left buccal corridor width (facial feature) LBCW and the right buccal corridor width (facial feature) RBCW of the patient based on a difference between (the third marking and the fifth marking) and (the sixth marking and the fourth marking), respectively, on the ruler of the secondary removably attachable tool 235 (Step 19). The measurements of the total smile width TSW, the left buccal corridor width LBCW, and the right buccal corridor width RBCW can provide valuable information regarding smile fullness and symmetry, which can contribute to the evaluation of smile aesthetics. It should be noted that the steps of obtaining the total smile width TSW, the left buccal corridor width LBCW, and the right buccal corridor width RBCW can occur in any order without departing from the present subject matter.

Figure 14:
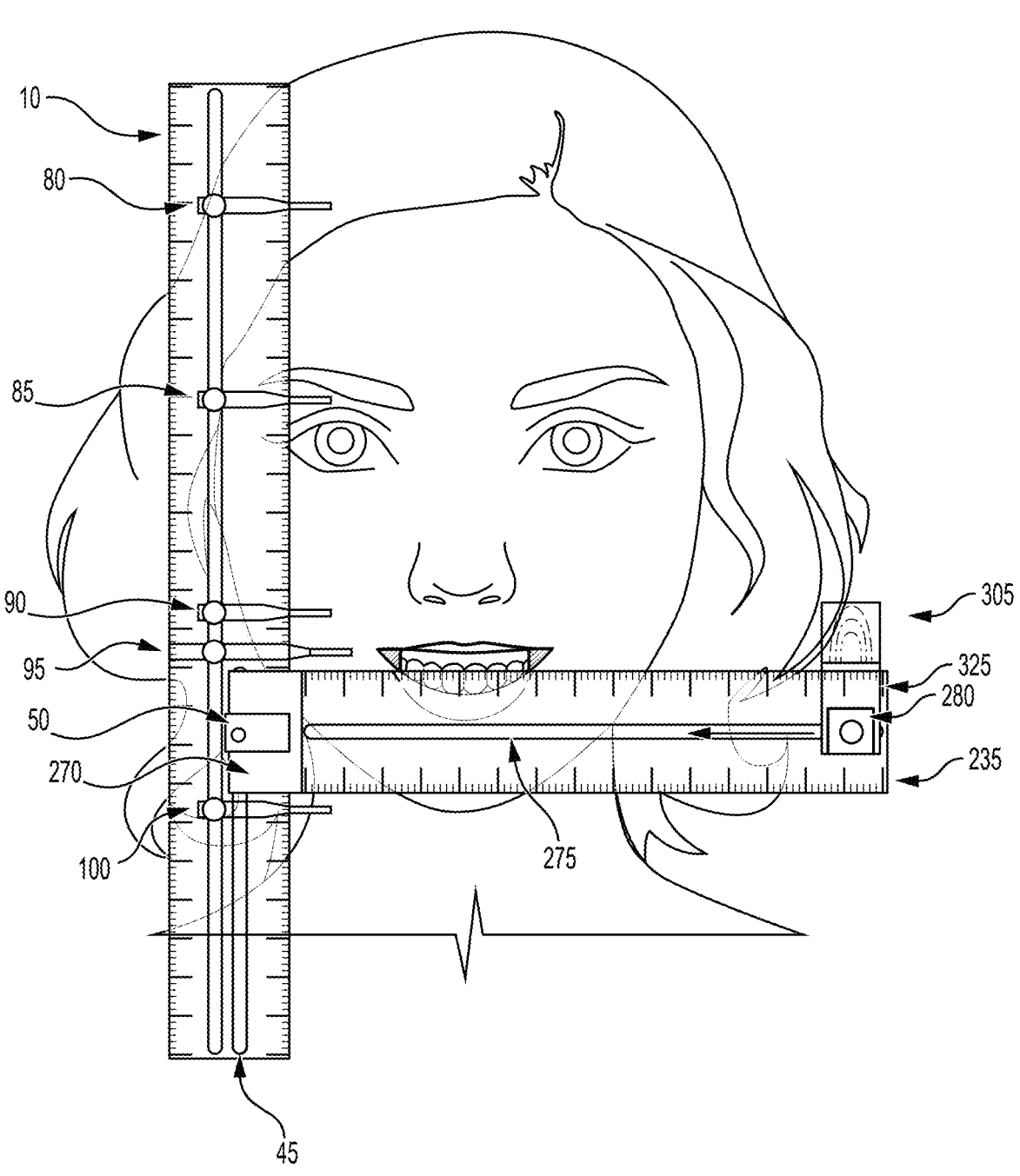
FIG. 14 depicts the attachment of the incisor proportion gauge to the secondary removably attachable tool.
Figure 15:
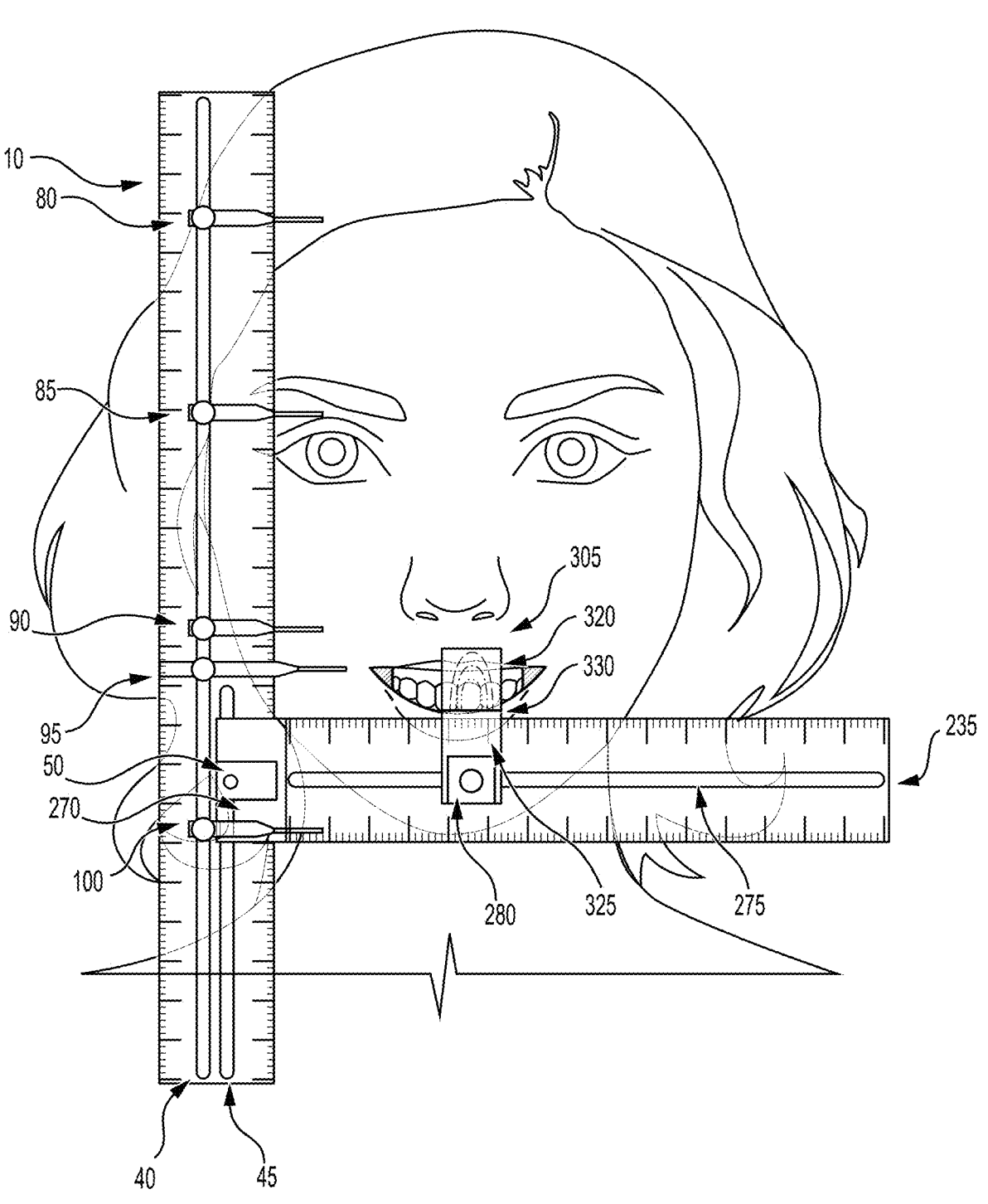
FIG. 15 depicts measuring the maxillary anterior teeth using the incisor proportion gauge.

Successively, the user can removably attach the incisor proportion gauge 305 to the secondary removably attachable tool 235 via the secondary transparent recess component 325 and the slidable secondary upper plate 280 as described supra and displayed in FIG. 14 (Step 20). Once attached and while the patient is still smiling, the user can slide the incisor proportion gauge 305 along the third slot 275 towards at least one of the maxillary anterior teeth 360 (see FIG. 12 for the location of the maxillary anterior teeth 360) as depicted in FIG. 15 (Step 21). It should be noted that during Step 21, the secondary removably attachable tool 235 can be positioned slightly below or adjacent to the fourth slidable pin 95, the left buccal (black) corridor 365, and the right buccal (black) corridor 370 as discussed supra (see Step 14).

Then, the user can align the incisal edge indicator line 330 of the incisor proportion gauge 305 at the incisal edge of the at least one of the maxillary anterior teeth 360 as shown in FIG. 15 (Step 21). After which, the user can determine which color-coded line (i.e., blue color, the green color, or the red color), as described above, best aligns with the shape of the one of the maxillary anterior teeth 360 as illustrated in FIG. 15 (Step 22). Next, the user can repeat Steps 21 and 22 for the rest of the at least one of the maxillary anterior teeth 360 (Step 23).

The color-coded lines can allow the user to compare the patient's natural dentition with idealized dimensions and evaluate each tooth (i.e., maxillary anterior teeth) proportion and symmetry. Additionally, the color-coded lines can facilitate assessment of the zenith line, the most apical point of the free gingival margin across the anterior teeth, which can be a crucial factor in gingival aesthetics and anterior smile design.

Referring back to FIG. 8, it should be noted that while the figure does not show the tool assembly 15 being placed in front of the patient's face initially, however it should be understood that the sole primary removably attachable tool 10 (including the components connected thereto as shown in FIG. 8) or the tool assembly 15 (as shown in FIG. 6) can be used initially to be placed in front of the patient's face without departing from the present subject matter. In this regard, if the tool assembly 15 is used initially instead of the sole primary removably attachable tool 10, then steps 1-12, 14-19, and 21-23 can be conducted for the former with the exclusion of steps 13 and 20.

All the data obtained from steps 1-23 procedure can be documented and stored for longitudinal assessment, interdisciplinary consultation, or treatment planning purposes. The procedure streamlines the process of facial and smile analysis while enhancing measurement accuracy and improving clinical efficiency. The tool assembly 15 offers a unified platform for facial and smile analysis, incorporating all essential diagnostic measurements into a single, versatile system. By enabling precise and efficient evaluation of facial height, smile width, lip mobility, and anterior tooth proportions, the tool assembly 15 supports a wide range of applications across dental and surgical disciplines (e.g., periodontology, oral and maxillofacial surgery, prosthodontics, and esthetic dentistry). The tool assembly's 15 modular architecture, ergonomic design, and ease of use make it a valuation tool for both routine clinical practice and advanced esthetic assessments.

It is to be understood that the method of measuring at least one facial feature of a patient using the tool assembly is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A tool assembly comprising:
a primary removably attachable tool comprising a first slot, a second slot, and a slidable primary upper plate removably attached to the second slot, wherein the slidable primary upper plate is configured to slide along the second slot;
a secondary removably attachable tool comprising a third slot and a slidable secondary upper plate removably attached to the third slot, the slidable secondary upper plate configured to slide along the third slot,
wherein the secondary removably attachable tool, attached to the slidable primary upper plate, is configured to slide along the second slot, and
wherein the first slot and the second slot of the primary removably attachable tool are parallel to each other, and wherein the third slot of the secondary removably attachable tool is perpendicular to the first slot and the second slot of the primary removably attachable tool.

2. The tool assembly of claim 1, wherein the primary removably attachable tool and/or the secondary removably attachable tool comprises a ruler.

3. The tool assembly of claim 1, wherein the primary removably attachable tool comprises a first portion, a second portion, a third portion, and a fourth portion, wherein an entire first length of the first slot extends within the second portion and the third portion of the primary removably attachable tool, and wherein an entire second length of the second slot extends within the second portion of the primary removably attachable tool.

4. The tool assembly of claim 1, wherein the secondary removably attachable tool comprises a first section, a second section, a third section, and a fourth section, wherein the first section of the secondary removably attachable tool comprises a primary transparent recess component, and wherein the attachment of the secondary removably attachable tool to the slidable primary upper plate is via the primary transparent recess component.

5. The tool assembly of claim 1, further comprising at least one slidable pin removably attached to the first slot of the primary removably attachable tool, and wherein the at least one slidable pin is configured to slide along the first slot.

6. The tool assembly of claim 5, wherein a portion of the at least one slidable pin is configured to be capable of sliding above and past the slidable primary upper plate.

7. The tool assembly of claim 6, wherein the at least one slidable pin comprises at least two of a first slidable pin, a second slidable pin, a third slidable pin, a fourth slidable pin, and a fifth slidable pin, and wherein each of the first slidable pin, the second slidable pin, the third slidable pin, the fourth slidable pin, and the fifth slidable pin are configured to be slidably positioned along various parts of a patient's face.

8. The tool assembly of claim 7, wherein the fourth slidable pin is longer than the first slidable pin, the second slidable pin, the third slidable pin, and the fifth slidable pin.

9. The tool assembly of claim 1, further comprising a gauge configured to be removably attached to the slidable secondary upper plate.

10. The tool assembly of claim 9, wherein the gauge comprises an incisor proportion gauge.

11. The tool assembly of claim 10, wherein the incisor proportion gauge comprises a secondary transparent recess component.

12. The tool assembly of claim 11, wherein the attachment of the incisor proportion gauge to the slidable secondary upper plate is via the secondary transparent recess component.

13. A method of using the tool assembly of claim 1 to measure at least one facial feature of a patient, the method comprising:
obtaining at least two slidable pins;
removably attaching the at least two slidable pins to the first slot of the primary removably attachable tool;
placing the tool assembly in front of the patient's face;
sliding a first of the at least two slidable pins along the first slot towards a first region of the patient's face;
sliding a second of the at least two slidable pins along the first slot towards a second region of the patient's face; and
measuring the at least one facial feature of the patient based on a height difference between the first of the at least two slidable pins and the second of the at least two slidable pins.

14. The method of claim 13, wherein the primary removably attachable tool and/or the secondary removably attachable tool comprises a ruler.

15. The method of claim 14, wherein the at least two slidable pins further comprise a third slidable pin, a fourth slidable pin, and a fifth slidable pin.

16. The method of claim 15, further comprising:
sliding the fourth slidable pin towards a first position of an upper lip line of the patient while the patient's mouth is at rest;
recording a first marking on the ruler of the primary removably attachable tool corresponding to the first position of the upper lip line of the patient;
sliding the fourth slidable pin towards a second position of the upper lip line of the patient after the patient has smiled;
recording a second marking on the ruler of the primary removably attachable tool corresponding to the second position of the upper lip line of the patient; and
measuring another of the at least one facial feature of the patient based on a height difference between the first marking and the second marking on the ruler.

17. The method of claim 16, further comprising:
sliding the secondary removably attachable tool near the patient's mouth as the slidable primary upper plate slides along the second slot;
recording a third marking and a fourth marking on the ruler of the secondary removably attachable tool corresponding to a right buccal corridor and a left buccal corridor, respectively, of the patient's mouth as the patient is smiling; and
measuring an additional of the at least one facial feature of the patient based on a difference between the third marking and the fourth marking on the ruler of the secondary removably attachable tool.

18. The method of claim 13, further comprising a gauge configured to be removably attached to the slidable secondary upper plate.

19. The method of claim 18, wherein the gauge comprises an incisor proportion gauge.

* * * * *